(12) United States Patent
Nishida et al.

(10) Patent No.: US 7,875,732 B2
(45) Date of Patent: Jan. 25, 2011

US007875732B2

(54) QUATERNARY AMMONIUM SALT, ELECTROLYTE, ELECTROLYTE, SOLUTION AND ELECTROCHEMICAL DEVICE

(75) Inventors: Tetsuo Nishida, Izumiotsu (JP); Kazutaka Hirano, Izumiotsu (JP); Megumi Tomisaki, Izumiotsu (JP); Yasutaka Tashiro, Izumiotsu (JP); Hitoshi Tsurumaru, Izumiotsu (JP); Akihiro Nabeshima, Tokushima (JP); Yoshinobu Abe, Tokushima (JP); Hiroaki Tokuda, Tokushima (JP); Akinori Oka, Tokushima (JP)

(73) Assignees: Otsuka Chemical Co., Ltd., Osaka (JP); Stella Chemifa Corporation, Osaka (JP)

( * ) Notice: Subject to any disclaimer, the term of this patent is extended or adjusted under 35 U.S.C. 154(b) by 722 days.

(21) Appl. No.: 11/795,036

(22) PCT Filed: Jan. 12, 2006

(86) PCT No.: PCT/JP2006/300664

§ 371 (c)(1),
(2), (4) Date: Jul. 11, 2007

(87) PCT Pub. No.: WO2006/077894

PCT Pub. Date: Jul. 27, 2006

(65) Prior Publication Data

US 2008/0050657 A1 Feb. 28, 2008

(30) Foreign Application Priority Data

Jan. 12, 2005 (JP) ............................ 2005-005768
Jan. 12, 2005 (JP) ............................ 2005-005789
Aug. 5, 2005 (JP) ............................ 2005-228320

(51) Int. Cl.
*C07D 207/08* (2006.01)

(52) U.S. Cl. ...................................................... 548/574

(58) Field of Classification Search ...................... None
See application file for complete search history.

(56) References Cited

U.S. PATENT DOCUMENTS

2003/0202316 A1 10/2003 Kawasato et al. ........... 361/502
2004/0094741 A1 5/2004 Sato et al. ....................... 252/1
2007/0042271 A1 2/2007 Nishida et al. .............. 429/306
2007/0099079 A1 5/2007 Matsumoto et al. ......... 429/188
2010/0038578 A1 * 2/2010 Nishida et al. ............. 252/62.2

FOREIGN PATENT DOCUMENTS

JP 10-55717 A 2/1998
JP 2004-006803 A 1/2004
WO 02/076924 A1 10/2002
WO 2005/003108 A1 1/2005
WO 2005/063773 A1 7/2005

OTHER PUBLICATIONS

Zhou, Zhi-Bin et al., "Low-melting, Low-viscous, Hydrophobic Ionic Liquids: *N*-Alkyl(alkyl ether)-*N*-methylpyrrolidinium Perfluoroethyltrifluoroborate", *Chemistry Letters*, vol. 33, No. 12 (2004) pp. 1636-1637.

* cited by examiner

*Primary Examiner*—Rebecca L Anderson
*Assistant Examiner*—Michael Barker
(74) *Attorney, Agent, or Firm*—Kubovcik & Kubovcik

(57) ABSTRACT

A quaternary ammonium salt of the formula (1)

(1)

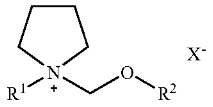

wherein $R^1$ is straight-chain or branched alkyl having 1 to 4 carbon atoms, $R^2$ is straight-chain or branched alkyl having 1 to 3 carbon atoms, and $X^-$ is $CF_3CO_2^-$, $CF_3SO_3BF_3^-$, $ClBF_3^-$, $AlF_4$—, $CF_3BF_3^-$, $C_2F_5BF_3$—, $N(SO_2F)_2^-$, $PF_6^-$, $AsF_6$— or $SbF_6^-$.

20 Claims, 4 Drawing Sheets

C···charge
D···discharge

QUATERNARY AMMONIUM SALT, ELECTROLYTE, ELECTROLYTE, SOLUTION AND ELECTROCHEMICAL DEVICE

This application is a 371 of international application PCT/JP2006/300664 filed Jan. 12, 2006, which claims priority based on Japanese patent application Nos. 2005-005768, 2005-005789 and 2005-228320 filed Jan. 12, Jan. 12 and Aug. 5, 2005, respectively, each of which is incorporated herein by reference.

TECHNICAL FIELD

The present invention relates to quaternary ammonium salts, electrolytes, electrolytic solutions and electrochemical devices. More particularly, the invention relates to functional materials which are usable as electrolytes having a high solubility in organic solvents, high voltage resistance and high electrical conductivity.

BACKGROUND ART

In recent years, higher output densities and improved energy densities have been required of electrochemical devices including cells and capacitors. Organic electrolytic solutions have found wider use than aqueous electrolytic solutions from the viewpoint of voltage resistance. Examples of organic electrolytic solutions are those prepared by dissolving alkali metal salts or solid ammonium salts in an organic solvent such as propylene carbonate. Electrolytic solutions of the former type are used for lithium ion cells, while those of the latter type are used for electric double-layer capacitors. Organic electrolytic solutions are inferior to aqueous solutions in electrical conductivity, and numerous studies have been made on organic solvents or electrolytes to obtain improved electrical conductivity.

The electrical conductivity of nonaqueous electrolytic solutions comprising such a solid electrolyte dissolved in a solvent varies with the concentration of the electrolyte. With a rise in the concentration, the ion concentration of the solution increases to increase the electrical conductivity, which will reach a maximum in due course. The electrical conductivity reaching the maximum starts to decrease presumably because the electrolyte becomes difficult to dissociate and increases in viscosity at the same time owing to increased interaction between the solvent and ions and between the ions as the number of ions increases in the electrolytic solution. When further increasing in concentration, the electrolyte becomes no longer dissociable, and the concentration of the electrolyte levels off. Thus, an attempt to increase the concentration of the electrolyte encounters the problem that the electrolyte becomes less soluble. Another problem is also experienced in that when electrolytic solutions having an electrolyte dissolved therein at a high concentration is used in an environment of low temperature, a salt will separate out to impair the electrical conductivity of the solution. Solvents of high dielectric constant are usually preferred for dissociating electrolytes to a higher degree, and propylene carbonate, ethylene carbonate, gamma-butyrolactone, etc. are in use. Suitable to use as electrolytes are tetraethylammonium tetrafluoroborate, triethylmethylammonium tetrafluoroborate and the like which are relatively soluble in solvents of high dielectric constant, whereas these electrolytes are limited in solubility to a concentration of about 2 M at room temperature and have the disadvantage of permitting separation of crystals when to be dissolved to higher concentrations or at lower temperatures. These electrolytes are almost insoluble in solvents of low dielectric constant, failing to form electrolytic solutions which are useful as such.

When propylene carbonate, ethylene carbonate, gamma-butyrolactone or the like is used as the solvent for applications necessitating a high voltage, the electrolyte is governed by the solvent decomposition voltage even if the electrolyte has high voltage resistance, with the result that the conventional capacitors are limited to about 2.5 V in operating voltage if highest. If the capacitor is operated at voltage exceeding 2.5 V, the electrolytic solution (mainly the solvent) undergoes electrochemical decomposition, becomes seriously impaired in performance and produces undesirable phenomena such as evolution of gas. In the application of capacitors as energy storage devices to mobile bodies such as hybrid cars and electric motor vehicles, improved energy capacities are demanded, and a higher operating voltage is effective means for giving an improved energy density, whereas it has been impossible to improve the voltage resistance with use of conventional electrolytic solutions, hence a need for electrolytes and solvents of higher voltage resistance. Since the electrostatic energy of capacitor is in proportion to square of voltage resistance, even a small improvement in voltage resistance is earnestly desired. Although chain carbonate solvents such as ethylmethyl carbonate, etc. are solvents of higher voltage resistance, conventional electrolytes such as tetraethylammonium tetrafluoroborate and triethylmethylammonium tetrafluoroborate are low in solubility in these solvents which are low in dielectric constant, and are not usable as electrolytic solutions.

Found in recent years are salts having a melting point around room temperature or salts having a melting point not higher than room temperature (salts melting at room temperature). It is known that even if solid at room temperature, such salts dissolve in organic solvents at a higher concentration than usual electrolytes. Furthermore, the salts melting at room temperature are miscible with a specific organic solvent in a desired ratio. Accordingly, these salts afford electrolytic solutions having a high concentration not available by dissolving conventional solid electrolytes in organic solvents, while although having a high concentration, the solution is less likely to encounter the problem that the salt will separate out in a low-temperature environment. The salt melting at room temperature is itself liquid and is therefore usable singly as an electrolyte.

It is disclosed that aliphatic ammonium salts having an alkoxyalkyl group introduced thereinto are highly soluble in a nonaqueous organic solvent and are less likely to separate out at low temperatures (patent literature 1).

However, in this literature, the salt melting at room temperature is evaluated as dissolved in propylene carbonate which is poor in voltage resistance.

As stated above, it is important to use a solvent having high voltage resistance in order to enhance energy density of capacitor. On the other hand, it is also effective to enhance electrical conductivity of electrolyte. Although capacitors can be, as one of their great characteristics, charged and discharged with a big electrical current compared with a secondary battery, energy loss due to resistance increases when the capacitor discharges with a big electrical current. To say extremely, even the energy is saved in the capacitor, most of the energy will be lost by resistance heat. Therefore, when the resistance is decreased in the capacitor, it is possible to enhance the energy which is substantially usable in the capacitor, and thus it is important to enhance electrical conductivity of electrolyte.

[patent literature 1] WO 02/076924

An object of the present invention is to provide an electrolyte which is not only highly electrically conductive but highly soluble in chain carbonic acid esters which is high in voltage resistance, highly reliable at low temperatures and high in voltage resistance, the invention further providing electrochemical device having such advantages.

DISCLOSURE OF THE INVENTION

The present invention provides the following inventions.

1. A quaternary ammonium salt of the formula (1)

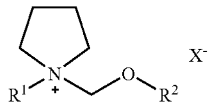

(1)

wherein $R^1$ is straight-chain or branched alkyl having 1 to 4 carbon atoms, $R^2$ is straight-chain or branched alkyl having 1 to 3 carbon atoms, and $X^-$ is $CF_3CO_2^-$, $CF_3SO_3BF_3^-$, $ClBF_3^-$, $AlF_4$—, $CF_3BF_3^-$, $C_2F_5BF_3$—, $N(SO_2F)_2^-$, $PF_6^-$, $AsF_6$— or $SbF_6^-$.

2. A quaternary ammonium salt of the formula (2)

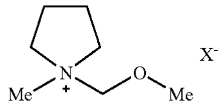

(2)

wherein $X^-$ is same as defined above, and Me is methyl.

3. A composition wherein the composition comprises at least one of quaternary ammonium salts of the formula (1) and the formula (2), and an organic solvent.

The present invention provides a quaternary ammonium salt of the formula (1), and an electrolytic solution containing the salt.

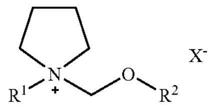

(1)

wherein $R^1$ is straight-chain or branched alkyl having 1 to 4 carbon atoms, $R^2$ is straight-chain or branched alkyl having 1 to 3 carbon atoms, and $X^-$ is $CF_3CO_2^-$, $CF_3CO_3BF_3^-$, $ClBF_3^-$, $AlF_4$—, $CF_3BF_3^-$, $C_2F_5BF_3$—, $N(SO_2F)_2^-$, $PF_6^-$, $AsF_6$— or $SbF_6^-$.

Examples of straight-chain or branched alkyl having 1 to 4 carbon atoms represented by $R^1$ are methyl, ethyl, n-propyl, iso-propyl, n-butyl, sec-butyl and tert-butyl. Preferable are straight-chain or branched alkyl having 1 to 3 carbon atoms. More preferable are methyl and ethyl.

Examples of straight-chain or branched alkyl having 1 to 3 carbon atoms represented by $R^2$ are methyl, ethyl, n-propyl and iso-propyl. Preferable are methyl and ethyl.

Examples of quaternary ammonium salts of the present invention are N-methoxymethyl-N-methylpyrrolidinium trifluoroacetate, N-ethyl-N-methoxymethylpyrrolidinium trifluoroacetate, N-methoxymethyl-N-n-propylpyrrolidinium trifluoroacetate, N-methoxymethyl-N-iso-propylpyrrolidinium trifluoroacetate, N-n-butyl-N-methoxymethylpyrrolidinium trifluoroacetate, N-iso-butyl-N-methoxymethylpyrrolidinium trifluoroacetate, N-tert-butyl-N-methoxymethylpyrrolidinium trifluoroacetate, N-methoxymethyl-N-methylpyrrolidinium trifluoromethane sulfonyltrifluoroborate, N-ethyl-N-methoxymethylpyrrolidinium trifluoromethane sulfonyltrifluoroborate, N-methoxymethyl-N-n-propylpyrrolidinium trifluoromethane sulfonyltrifluoroborate, N-methoxymethyl-N-iso-propylpyrrolidinium trifluoromethane sulfonyltrifluoroborate, N-n-butyl-N-methoxymethyl-pyrrolidinium trifluoromethane sulfonyltrifluoroborate, N-iso-butyl-N-methoxymethylpyrrolidinium trifluoromethane sulfonyltrifluoroborate, N-tert-butyl-N-methoxymethylpyrrolidinium trifluoromethane sulfonyltrifluoroborate, N-methoxymethyl-N-methylpyrrolidinium chlorotrifluoroborate, N-ethyl-N-methoxymethylpyrrolidinium chlorotrifluoroborate, N-methoxymethyl-N-n-propylpyrrolidinium chlorotrifluoroborate, N-methoxymethyl-N-iso-propylpyrrolidinium chlorotrifluoroborate, N-n-butyl-N-methoxymethylpyrrolidinium chlorotrifluoroborate, N-iso-butyl-N-methoxymethylpyrrolidinium chlorotrifluoroborate, N-tert-butyl-N-methoxymethylpyrrolidinium chlorotrifluoroborate, N-methoxymethyl-N-methylpyrrolidinium tetrafluoroaluminate, N-ethyl-N-methoxymethylpyrrolidinium tetrafluoroaluminate, N-methoxymethyl-N-n-propylpyrrolidinium tetrafluoroaluminate, N-methoxymethyl-N-iso-propylpyrrolidinium tetrafluoroaluminate, N-n-butyl-N-methoxymethylpyrrolidinium N-iso-butyl-N-methoxymethylpyrrolidinium tetrafluoroaluminate, N-tert-butyl-N-methoxymethylpyrrolidinium tetrafluoroaluminate, N-methoxymethyl-N-methylpyrrolidinium trifluoromethyltrifluoroborate, N-ethyl-N-methoxymethylpyrrolidinium trifluoromethyltrifluoroborate, N-methoxymethyl-N-n-propylpyrrolidinium trifluoromethyltrifluoroborate, N-methoxymethyl-N-iso-propylpyrrolidinium trifluoromethyl-trifluoroborate, N-n-butyl-N-methoxymethylpyrrolidinium trifluoromethyltrifluoroborate, N-iso-butyl-N-methoxymethyl-pyrrolidinium trifluoromethyltrifluoroborate, N-tert-butyl-N-methoxymethylpyrrolidinium trifluoromethyltrifluoroborate, N-methoxymethyl-N-methylpyrrolidinium pentafluoroethyl trifluoroborate, N-ethyl-N-methoxymethylpyrrolidinium pentafluoroethyl trifluoroborate, N-methoxymethyl-N-n-propylpyrrolidinium pentafluoroethyl trifluoroborate, N-methoxymethyl-N-iso-propylpyrrolidinium pentafluoroethyl trifluoroborate, N-n-butyl-N-methoxymethylpyrrolidinium pentafluoroethyl trifluoroborate, N-iso-butyl-N-methoxymethylpyrrolidinium pentafluoroethyl trifluoroborate, N-tert-butyl-N-methoxymethylpyrrolidinium pentafluoroethyl trifluoroborate, N-methoxymethyl-N-methylpyrrolidinium bis(fluorosulfonyl)imide, N-ethyl-N-methoxymethyl-pyrrolidinium bis(fluoroslufonyl)imide, N-methoxymethyl-N-n-propylpyrrolidinium bis(fluorosulfonyl) imide, N-methoxy-methyl-N-iso-propylpyrrolidinium bis (fluorosulfonyl)imide, N-n-butyl-N-methoxymethylpyrrolidinium bis(fluorosulfonyl)-imide, N-iso-butyl-N-methoxymethylpyrrolidinium bis(fluorosulfonyl)imide, N-tert-butyl-N-methoxymethyl-pyrrolidinium bis(fluorosulfonyl)imide, N-ethoxymethyl-N-methylpyrrolidinium trifluoroacetate, N-ethoxymethyl-N-ethylpyrrolidinium trifluoroacetate, N-ethoxymethyl-N-n-propylpyrrolidinium trifluoroacetate, N-ethoxymethyl-N-isopropylpyrrolidinium trifluoroacetate, N-n-butyl-N-ethoxymethylpyrrolidinium trifluoroacetate, N-iso-butyl-N-ethoxymethylpyrrolidinium trifluoroacetate, N-tert-butyl-N-ethoxymethylpyrrolidinium trifluoroacetate, N-ethoxymethyl-N-methylpyrrolidinium trifluoromethane sulfonyltrifluoroborate, N-ethoxymethyl-N-ethylpyrrolidinium trifluoromethane sulfonyltrifluoroborate, N-ethoxymethyl-N-n-propyl-pyrrolidinium trifluoromethane sulfonyltrifluoroborate, N-ethoxymethyl-N-iso-propylpyrrolidinium trifluoromethane sulfonyltrifluoroborate, N-n-butyl-N-ethoxymethyl-pyrrolidinium trifluoromethane sulfonyltrifluoroborate, N-iso-butyl-N-ethoxymethylpyrrolidinium trifluoromethane sulfonyltrifluoroborate, N-tert-butyl-N-ethoxymethyl-pyrrolidinium trifluoromethane sulfonyltrifluoroborate, N-ethoxymethyl-N-methylpyrrolidinium chlorotrifluoroborate, N-ethoxymethyl-N-ethylpyrrolidinium chlorotrifluoroborate, N-ethoxymethyl-N-n-propylpyrrolidinium chlorotrifluoroborate, N-ethoxymethyl-N-iso-propylpyrrolidinium chlorotrifluoroborate, N-n-butyl-N-ethoxymethylpyrrolidinium chlorotrifluoroborate, N-iso-butyl-N-ethoxymethylpyrrolidinium chlorotrifluoroborate, N-tert-butyl-N-ethoxymethylpyrrolidinium chlorotrifluoroborate, N-ethoxymethyl-N-methylpyrrolidinium tetrafluoroaluminate, N-ethoxymethyl-N-ethylpyrrolidinium tetrafluoroaluminate, N-ethoxymethyl-N-n-propylpyrrolidinium tetrafluoroaluminate, N-ethoxymethyl-N-iso-propylpyrrolidinium tetrafluoroaluminate, N-n-butyl-N-ethoxymethylpyrrolidinium tetrafluoroaluminate, N-iso-butyl-N-ethoxymethylpyrrolidinium tetrafluoroaluminate, N-tert-butyl-N-ethoxymethylpyrrolidinium tetrafluoroaluminate, N-ethoxymethyl-N-methylpyrrolidinium trifluoromethyl trifluoroborate, N-ethoxymethyl-N-ethylpyrrolidinium trifluoromethyl trifluoroborate, N-ethoxymethyl-N-n-propylpyrrolidinium trifluoromethyl trifluoroborate, N-ethoxymethyl-N-iso-propylpyrrolidinium trifluoromethyl trifluoroborate, N-n-butyl-N-ethoxymethylpyrrolidinium trifluoromethyl trifluoroborate, N-iso-butyl-N-ethoxymethylpyrrolidinium trifluoromethyl trifluoroborate, N-tert-butyl-N-ethoxymethylpyrrolidinium trifluoromethyl trifluoroborate, N-ethoxymethyl-N-methylpyrrolidinium pentafluoroethyl trifluoroborate, N-ethoxymethyl-N-ethylpyrrolidinium pentafluoroethyl trifluoroborate, N-ethoxymethyl-N-n-propylpyrrolidinium pentafluoroethyl trifluoroborate, N-ethoxymethyl-N-iso-propylpyrrolidinium pentafluoroethyl trifluoroborate, N-n-butyl-N-ethoxymethylpyrrolidinium pentafluoroethyl trifluoroborate, N-iso-butyl-N-ethoxymethylpyrrolidinium pentafluoroethyl trifluoroborate, N-tert-butyl-N-ethoxymethylpyrrolidinium pentafluoroethyl trifluoroborate, N-ethoxymethyl-N-methylpyrrolidinium bis(fluorosulfonyl)imide, N-ethoxymethyl-N-ethylpyrrolidinium bis(fluoroslufonyl)imide, N-ethoxymethyl-N-n-propylpyrrolidinium bis(fluorosulfonyl)imide, N-ethoxymethyl-N-iso-propylpyrrolidinium bis(fluorosulfonyl)-imide, N-n-butyl-N-ethoxymethylpyrrolidinium bis(fluorosulfonyl)imide, N-iso-butyl-N-ethoxymethylpyrrolidinium bis(fluorosulfonyl)imide, N-tert-butyl-N-ethoxymethylpyrrolidinium bis(fluorosulfonyl)imide, N-methyl-N-n-propoxymethylpyrrolidinium trifluoroacetate, N-ethyl-N-n-propoxymethylpyrrolidinium trifluoroacetate, N-n-propyl-N-n-propoxymethylpyrrolidinium trifluoroacetate, N-iso-propyl-N-n-propoxymethylpyrrolidinium trifluoroacetate, N-n-butyl-N-n-propoxymethylpyrrolidinium trifluoroacetate, N-iso-butyl-N-n-propoxymethylpyrrolidinium trifluoroacetate, N-tert-butyl-N-n-propoxymethylpyrrolidinium trifluoroacetate, N-methyl-N-n-propoxymethylpyrrolidinium trifluoromethane sulfonyltrifluoroborate, N-ethyl-N-n-propoxymethylpyrrolidinium trifluoromethane sulfonyltrifluoroborate, N-n-propyl-N-n-propoxymethylpyrrolidinium trifluoromethane sulfonyltrifluoroborate, N-iso-propyl-N-n-propoxymethylpyrrolidinium trifluoromethane sulfonyltrifluoroborate, N-n-butyl-N-n-propoxymethylpyrrolidinium trifluoromethane sulfonyltrifluoroborate, N-iso-butyl-N-n-propoxymethylpyrrolidinium trifluoromethane sulfonyltrifluoroborate, N-tert-butyl-N-n-propoxymethylpyrrolidinium trifluoromethane sulfonyltrifluoroborate, N-methyl-N-n-propoxymethylpyrrolidinium chlorotrifluoroborate, N-ethyl-N-n-propoxymethylpyrrolidinium chlorotrifluoroborate, N-n-propyl-N-n-propoxymethylpyrrolidinium chlorotrifluoroborate, N-iso-propyl-N-n-propoxymethylpyrrolidinium chlorotrifluoroborate, N-n-butyl-N-n-propoxymethylpyrrolidinium chlorotrifluoroborate, N-iso-butyl-N-n-propoxymethylpyrrolidinium chlorotrifluoroborate, N-tert-butyl-N-n-propoxymethylpyrrolidinium chlorotrifluoroborate, N-methyl-N-n-propoxymethylpyrrolidinium tetrafluoroaluminate, N-ethyl-N-n-propxymethylpyrrolidinium tetrafluoroaluminate, N-n-propyl-N-n-propoxymethylpyrrolidinium tetrafluoroaluminate, N-iso-propyl-N-n-propoxymethylpyrrolidinium tetrafluoroaluminate, N-n-butyl-N-n-propoxymethylpyrrolidinium tetrafluoroaluminate, N-iso-butyl-N-n-propoxymethylpyrrolidinium tetrafluoroaluminate, N-tert-butyl-N-propoxymethylpyrrolidinium tetrafluoroaluminate, N-methyl-N-n-propoxymethylpyrrolidinium trifluoromethyl trifluoroborate, N-ethyl-N-n-propoxymethylpyrrolidinium trifluoromethyl trifluoroborate, N-n-propyl-N-n-propoxymethylpyrrolidinium trifluoromethyl trifluoroborate, N-iso-propyl-N-n-propoxymethylpyrrolidinium trifluoromethyl trifluoroborate, N-n-butyl-N-n-propoxymethylpyrrolidinium trifluoromethyl trifluoroborate, N-iso-butyl-N-n-propoxymethylpyrrolidinium tetrafluoroaluminate, N-tert-butyl-N-propoxymethylpyrrolidinium trifluoromethyl trifluoroborate, N-methyl-N-n-propoxymethylpyrrolidinium pentafluoroethyl trifluoroborate, N-ethyl-N-n-propoxymethylpyrrolidinium pentafluoroethyl trifluoroborate, N-n-propyl-N-n-propoxymethylpyrrolidinium pentafluoroethyl trifluoroborate, N-iso-propyl-N-n-propoxymethylpyrrolidinium pentafluoroethyl trifluoroborate, N-n-butyl-N-n-propoxymethylpyrrolidinium pentafluoroethyl trifluoroborate, N-iso-butyl-N-n-propoxymethylpyrrolidinium pentafluoroethyl trifluoroborate, N-tert-butyl-N-propoxymethylpyrrolidinium pentafluoromethyl trifluoroborate, N-methyl-N-n-propoxymethylpyrrolidinium bis(fluorosulfonyl)-imide, N-ethyl-N-n-propoxymethylpyrrolidinium bis(fluoroslufonyl)imide, N-n-propyl-N-n-propoxymethylpyrrolidinium bis(fluorosulfonyl)imide, N-iso-propyl-N-n-propoxymethylpyrrolidinium bis(fluorosulfonyl)imide, N-n-butyl-N-n-propoxymethylpyrrolidinium bis(fluorosulfonyl)-imide, N-iso-butyl-N-n-propoxymethylpyrrolidinium bis(fluorosulfonyl)imide, N-tert-butyl-N-n-propoxymethylpyrrolidinium bis(fluorosulfonyl)imide, N-methyl-N-iso-propoxymethylpyrrolidinium trifluoroacetate, N-ethyl-N-iso-propoxymethylpyrrolidinium trifluoroacetate, N-n-propyl-N-iso-propoxymethylpyrrolidinium trifluoroacetate, N-iso-propyl-N-iso-propoxymethylpyrrolidinium trifluoroacetate, N-n-butyl-N-iso-propoxymethylpyrrolidinium trifluoroacetate, N-iso-butyl-N-iso-propoxymethylpyrrolidinium trifluoroacetate, N-tert-butyl-N-iso-propoxymethylpyrrolidinium trifluoroacetate, N-methyl-N-iso-propoxymethylpyrrolidinium trifluoromethane sulfonyltrifluoroborate, N-ethyl-N-iso-propoxymethylpyrrolidinium trifluoromethane sulfonyltrifluoroborate, N-n-propyl-N-iso-propoxymethylpyrrolidinium trifluoromethane sulfonyltrifluoroborate, N-iso-propyl-N-iso-propoxymethylpyrrolidinium trifluoromethane sulfonyltrifluoroborate, N-n-butyl-N-iso-propoxymethylpyrrolidinium trifluoromethane sulfonyltrifluoroborate, N-iso-butyl-N-iso-propoxymethylpyrrolidinium trifluoromethane sulfonyltrifluoroborate, N-tert-butyl-N-iso-propoxymethylpyrrolidinium trifluoromethane sulfonyltrifluoroborate, N-methyl-N-iso-propoxymethylpyrrolidinium chlorotrifluoroborate, N-ethyl-N-iso-propoxymethylpyrrolidinium chlorotrifluoroborate, N-n-propyl-N-iso-propoxymethylpyrrolidinium chlorotrifluoroborate, N-iso-propyl-N-iso-propoxymethylpyrrolidinium chlorotrifluoroborate, N-n-butyl-N-iso-propoxymethylpyrrolidinium chlorotrifluoroborate, N-iso-butyl-N-iso-propoxymethylpyrrolidinium chloro-trifluoroborate, N-tert-butyl-N-iso-propoxymethylpyrrolidinium chlorotrifluoroborate, N-methyl-N-iso-propoxymethylpyrrolidinium tetrafluoroaluminate, N-ethyl-N-iso-propxymethylpyrrolidinium tetrafluoroaluminate, N-n-propyl-N-iso-propoxymethylpyrrolidinium tetrafluoroaluminate, N-iso-propyl-N-iso-propoxymethylpyrrolidinium tetrafluoro-aluminate, N-n-butyl-N-iso-propoxymethylpyrrolidinium tetrafluoroaluminate, N-iso-butyl-N-iso-propoxymethylpyrrolidinium tetrafluoroaluminate, N-tert-butyl-N-iso-propoxymethylpyrrolidinium tetrafluoroaluminate, N-methyl-N-iso-propoxymethylpyrrolidinium trifluoromethyl trifluoroborate, N-ethyl-N-iso-propoxymethylpyrrolidinium trifluoromethyl trifluoroborate, N-n-propyl-N-iso-propoxymethylpyrrolidinium trifluoromethyl trifluoroborate, N-iso-propyl-N-iso-propoxymethylpyrrolidinium trifluoromethyl trifluoroborate, N-n-butyl-N-iso-propoxymethylpyrrolidinium trifluoromethyl trifluoroborate, N-iso-butyl-N-iso-propoxymethylpyrrolidinium trifluoromethyl trifluoroborate, N-tert-butyl-N-iso-propoxymethylpyrrolidinium trifluoromethyl trifluoroborate, N-methyl-N-iso-propoxymethylpyrrolidinium pentafluoroethyl trifluoroborate, N-ethyl-N-iso-propoxymethylpyrrolidinium pentafluoroethyl trifluoroborate, N-n-propyl-N-iso-propoxymethylpyrrolidinium pentafluoroethyl trifluoroborate, N-iso-propyl-N-iso-propoxymethylpyrrolidinium pentafluoroethyl trifluoroborate, N-n-butyl-N-iso-propoxymethylpyrrolidinium pentafluoroethyl trifluoroborate, N-iso-butyl-N-iso-propoxymethylpyrrolidinium pentafluoroethyl trifluoroborate, N-tert-butyl-N-iso-propoxymethylpyrrolidinium pentafluoroethyl trifluoroborate, N-methyl-N-iso-propoxymethylpyrrolidinium bis(fluorosulfonyl)imide, N-ethyl-N-iso-propoxymethylpyrrolidinium bis(fluoroslufonyl)imide, N-n-propyl-N-iso-propoxymethylpyrrolidinium bis(fluorosulfonyl)imide, N-iso-propyl-N-iso-propoxymethylpyrrolidinium bis(fluorosulfonyl)-imide, N-n-butyl-N-iso-propoxymethylpyrrolidinium bis(fluorosulfonyl)imide, N-iso-butyl-N-iso-propoxymethylpyrrolidinium bis(fluorosulfonyl)imide, N-tert-butyl-N-iso-propoxymethylpyrrolidinium bis(fluorosulfonyl)imide, N-methoxymethyl-N-methylpyrrolidinium hexafluorophosphate, N-ethyl-N-methoxymethylpyrrolidinium hexafluorophosphate, N-methoxymethyl-N-n-propylpyrrolidinium hexafluorophosphate, N-methoxymethyl-N-iso-propylpyrrolidinium hexafluorophosphate, N-n-butyl-N-methoxymethylpyrrolidinium hexafluorophosphate, N-iso-butyl-N-methoxymethylpyrrolidinium hexafluorophosphate, N-tert-butyl-N-methoxymethylpyrrolidinium hexafluorophosphate, N-methoxymethyl-N-methylpyrrolidinium hexafluoroarsenate, N-ethyl-N-methoxymethylpyrrolidinium hexafluoroarsenate, N-methoxymethyl-N-n-propylpyrrolidinium hexafluoroarsenate, N-methoxymethyl-N-iso-propylpyrrolidinium hexafluoroarsenate, N-n-butyl-N-methoxymethylpyrrolidinium hexafluoroarsenate, N-iso-butyl-N-methoxymethylpyrrolidinium hexafluoroarsenate, N-tert-butyl-N-methoxymethylpyrrolidinium hexafluoroarsenate, N-methoxymethyl-N-methylpyrrolidinium hexafluoroantimonate, N-ethyl-N-methoxymethylpyrrolidinium hexafluoroantimonate, N-methoxymethyl-N-n-propylpyrrolidinium hexafluoroantimonate, N-methoxymethyl-N-iso-propylpyrrolidinium hexafluoroantimonate, N-n-butyl-N-methoxymethylpyrrolidinium hexafluoroantimonate, N-iso-butyl-N-methoxymethylpyrrolidinium hexafluoroantimonate, N-tert-butyl-N-methoxymethylpyrrolidinium hexafluoroantimonate, N-ethoxymethyl-N-methylpyrrolidinium hexafluorophosphate, N-ethoxymethyl-N-ethylpyrrolidinium hexafluorophosphate, N-ethoxymethyl-N-n-propylpyrrolidinium hexafluorophosphate, N-ethoxymethyl-N-iso-propylpyrrolidinium hexafluorophosphate, N-n-butyl-N-ethoxymethylpyrrolidinium hexafluorophosphate, N-iso-butyl-N-ethoxymethylpyrrolidinium hexafluorophosphate, N-tert-butyl-N-ethoxymethylpyrrolidinium hexafluorophosphate, N-ethoxymethyl-N-methylpyrrolidinium hexafluoroarsenate, N-ethoxymethyl-N-ethylpyrrolidinium hexafluoroarsenate, N-ethoxymethyl-N-n-propylpyrrolidinium hexafluoroarsenate, N-ethoxymethyl-N-iso-propylpyrrolidinium hexafluoroarsenate, N-n-butyl-N-ethoxymethylpyrrolidinium hexafluoroarsenate, N-iso-butyl-N-ethoxymethylpyrrolidinium hexafluoroarsenate, N-tert-butyl-N-ethoxymethylpyrrolidinium hexafluoroarsenate, N-ethoxymethyl-N-methylpyrrolidinium hexafluoroantimonate, N-ethoxymethyl-N-ethylpyrrolidinium hexafluoroantimonate, N-ethoxymethyl-N-n-propylpyrrolidinium hexafluoroantimonate, N-ethoxymethyl-N-iso-propylpyrrolidinium hexafluoroantimonate, N-n-butyl-N-ethoxymethylpyrrolidinium hexafluoroantimonate, N-iso-butyl-N-ethoxymethylpyrrolidinium hexafluoroantimonate, N-tert-butyl-N-ethoxymethylpyrrolidinium hexafluoroantimonate, N-methyl-N-n-propoxymethylpyrrolidinium hexafluorophosphate, N-ethyl-N-n-propoxymethylpyrrolidinium hexafluorophosphate, N-n-propyl-N-n-propoxymethylpyrrolidinium hexafluorophosphate, N-iso-propyl-N-n-propoxymethylpyrrolidinium hexafluorophosphate, N-n-butyl-N-n-propoxymethylpyrrolidinium hexafluorophosphate, N-iso-butyl-N-n-propoxymethylpyrrolidinium hexafluorophosphate, N-tert-butyl-N-n-propoxymethylpyrrolidinium hexafluorophosphate, N-methyl-N-n-propoxymethylpyrrolidinium hexafluoroarsenate, N-ethyl-N-n-propoxymethylpyrrolidinium hexafluoroarsenate, N-n-propyl-N-n-propoxymethylpyrrolidinium hexafluoroarsenate, N-iso-propyl-N-n-propoxymethylpyrrolidinium hexafluoroarsenate, N-n-butyl-N-n-propoxymethylpyrrolidinium hexafluoroarsenate, N-iso-butyl-N-n-propoxymethylpyrrolidinium hexafluoroarsenate, N-tert-butyl-N-n-propoxymethylpyrrolidinium hexafluoroarsenate, N-methyl-N-n-propoxymethylpyrrolidinium hexafluoroantimonate, N-ethyl-N-n-propoxymethylpyrrolidinium hexafluoroantimonate, N-n-propyl-N-n-propoxymethylpyrrolidinium hexafluoroantimonate, N-iso-propyl-N-n-propoxymethylpyrrolidinium hexafluoroantimonate, N-n-butyl-N-n-propoxymethylpyrrolidinium hexafluoroantimonate, N-iso-butyl-N-n-propoxymethylpyrrolidinium hexafluoroantimonate, N-tert-butyl-N-n-propoxymethylpyrrolidinium hexafluoroantimonate, N-methyl-N-iso-propoxymethylpyrrolidinium hexafluorophosphate, N-ethyl-N-iso-propoxymethylpyrrolidinium hexafluorophosphate, N-n-propyl-N-n-propoxymethylpyrrolidinium hexafluorophosphate, N-iso-propyl-N-iso-propoxymethylpyrrolidinium hexafluorophosphate, N-n-butyl-N-iso-propoxymethylpyrrolidinium hexafluorophosphate, N-iso-butyl-N-iso-propoxymethylpyrrolidinium hexafluorophosphate, N-tert-butyl-N-iso-propoxymethylpyrrolidinium hexafluorophosphate, N-methyl-N-iso-propoxymethylpyrrolidinium hexafluoroarsenate, N-ethyl-N-iso-propoxymethylpyrrolidinium hexafluoroarsenate, N-n-propyl-N-iso-propoxymethylpyrrolidinium hexafluoroarsenate, N-iso-propyl-N-iso-propoxymethylpyrrolidinium hexafluoroarsenate, N-n-butyl-N-iso-propoxymethylpyrrolidinium hexafluoroarsenate, N-iso-butyl-N-iso-propoxymethylpyrrolidinium hexafluoroarsenate, N-tert-butyl-N-iso-propoxymethylpyrrolidinium hexafluoroarsenate, N-methyl-N-iso-propoxymethylpyrrolidinium hexafluoroantimonate, N-ethyl-N-iso-propoxymethylpyrrolidinium hexafluoroantimonate, N-n-propyl-N-iso-propoxymethylpyrrolidinium hexafluoroantimonate, N-iso-propyl-N-iso-propoxymethylpyrrolidinium hexafluoroantimonate, N-n-butyl-N-iso-propoxymethylpyrrolidinium hexafluoroantimonate, N-iso-butyl-N-iso-propoxymethylpyrrolidinium hexafluoroantimonate and N-tert-butyl-N-iso-propoxymethylpyrrolidinium hexafluoroantimonate.

Preferable are N-methoxymethyl-N-methylpyrrolidinium trifluoroacetate, N-ethyl-N-methoxymethylpyrrolidinium trifluoroacetate, N-ethoxymethyl-N-methylpyrrolidinium trifluoroacetate and N-ethoxymethyl-N-ethylpyrrolidinium trifluoroacetate.

Preferable are N-methoxymethyl-N-methylpyrrolidinium trifluoromethane sulfonyltrifluoroborate, N-ethyl-N-methoxymethylpyrrolidinium trifluoromethane sulfonyltrifluoroborate, N-ethoxymethyl-N-methylpyrrolidinium trifluoromethane sulfonyltrifluoroborate, and N-ethoxymethyl-N-ethylpyrrolidinium trifluoromethane sulfonyltrifluoroborate.

Preferable are N-methoxymethyl-N-methylpyrrolidinium chlorotrifluoroborate, N-ethyl-N-methoxymethylpyrrolidinium chlorotrifluoroborate, N-ethoxymethyl-N-methylpyrrolidinium chlorotrifluoroborate, and N-ethoxymethyl-N-ethylpyrrolidinium chlorotrifluoroborate.

Preferable are N-methoxymethyl-N-methylpyrrolidinium tetrafluoroaluminate, N-ethyl-N-methoxymethylpyrrolidinium tetrafluoroaluminate, N-ethoxymethyl-N-methylpyrrolidinium tetrafluoroaluminate and N-ethoxymethyl-N-ethylpyrrolidinium tetrafluoroaluminate.

Preferable are N-methoxymethyl-N-methylpyrrolidinium trifluoromethyl trifluoroborate, N-ethyl-N-methoxymethylpyrrolidinium trifluoromethyl trifluoroborate, N-ethoxymethyl-N-methylpyrrolidinium trifluoromethyl trifluoroborate and N-ethoxymethyl-N-ethylpyrrolidinium trifluoromethyl trifluoroborate.

Preferable are N-methoxymethyl-N-methylpyrrolidinium pentafluoroethyl trifluoroborate, N-ethyl-N-methoxymethylpyrrolidinium pentafluoroethyl trifluoroborate, N-ethoxymethyl-N-methylpyrrolidinium pentafluoroethyl trifluoroborate and N-ethoxymethyl-N-pentafluoroethyl trifluoroborate.

Preferable are N-methoxymethyl-N-methylpyrrolidinium bis(fluorosulfonyl)imide, N-ethyl-N-methoxymethylpyrrolidinium bis(fluorosulfonyl)imide, N-ethoxymethyl-N-methylpyrrolidinium bis(fluorosulfonyl)imide and N-ethoxymethyl-N-ethylpyrrolidinium bis(fluorosulfonyl)imide.

More preferable are N-methoxymethyl-N-methylpyrrolidinium trifluoroacetate and N-ethoxymethyl-N-methylpyrrolidinium trifluoroacetate.

More preferable are N-methoxymethyl-N-methylpyrrolidinium trifluoromethane sulfonyltrifluoroborate and N-ethoxymethyl-N-methylpyrrolidinium trifluoromethane sulfonyltrifluoroborate.

More preferable are N-methoxymethyl-N-methylpyrrolidinium chlorotrifluoroborate, and N-ethoxymethyl-N-methylpyrrolidinium chlorotrifluoroborate.

More preferable are N-methoxymethyl-N-methylpyrrolidinium tetrafluoroaluminate and N-ethoxymethyl-N-methylpyrrolidinium tetrafluoroaluminate.

More preferable are N-methoxymethyl-N-methylpyrrolidinium trifluoromethyl trifluoroborate and N-ethoxymethyl-N-methylpyrrolidinium trifluoromethyl trifluoroborate.

More preferable are N-methoxymethyl-N-methylpyrrolidinium pentafluoroethyl trifluoroborate and N-ethoxymethyl-N-methylpyrrolidinium pentafluoroethyl trifluoroborate.

More preferable are N-methoxymethyl-N-methylpyrrolidinium bis(fluorosulfonyl)imide and N-ethoxymethyl-N-ethylpyrrolidinium bis(fluorosulfonyl)imide.

Preferable are N-methoxymethyl-N-methylpyrrolidinium hexafluorophosphate, N-ethyl-N-methoxymethylpyrrolidinium hexafluorophosphate, N-ethoxymethyl-N-methylpyrrolidinium hexafluorophosphate and N-ethoxymethyl-N-ethylpyrrolidinium hexafluorophosphate.

Preferable are N-methoxymethyl-N-methylpyrrolidinium hexafluoroarsenate, N-ethyl-N-methoxymethylpyrrolidinium hexafluoroarsenate, N-ethoxymethyl-N-methylpyrrolidinium hexafluoroarsenate and N-ethoxymethyl-N-ethylpyrrolidinium hexafluoroarsenate.

Preferable are N-methoxymethyl-N-methylpyrrolidinium hexafluoroantimonate, N-ethyl-N-methoxymethylpyrrolidinium hexafluoroantimonate, N-ethoxymethyl-N-methylpyrrolidinium hexafluoroantimonate and N-ethoxymethyl-N-ethylpyrrolidinium hexafluoroantimonate.

More preferable are N-methoxymethyl-N-methylpyrrolidinium hexafluorophosphate and N-ethoxymethyl-N-methylpyrrolidinium hexafluorophosphate.

More preferable are N-methoxymethyl-N-methylpyrrolidinium hexafluoroarsenate and N-ethoxymethyl-N-methylpyrrolidinium hexafluoroarsenate.

More preferable are N-methoxymethyl-N-methylpyrrolidinium hexafluoroantimonate and ethoxymethyl-N-methylpyrrolidinium hexafluoroantimonate.

When $X^-$ is $CF_3CO_2^-$, $CF_3SO_3BF_3^-$, $ClBF_3^-$, $AlF_4$—, $CF_3BF_3^-$, $C_2F_5BF_3$— or $N(SO_2F)_2^-$, the present quaternary ammonium salt is liquid at an ordinary temperature (25° C.). Further, the salt is excellent in solubility in an organic solvent, especially in chain carbonic acid ester, and does not form a crystal at a low temperature (for example, 0° C.).

When, $X^-$ is $PF_6^-$, $AsF_6$— or $SbF_6^-$, the present quaternary ammonium salt is solid at an ordinary temperature (25° C.). The salt is more excellent in solubility in an organic solvent, especially in chain carbonic acid ester, than the above salt.

The quaternary ammonium salt of the present invention can be prepared by various processes. Typical of these processes are represented by Equation-1 and Equation-2 given below.

Preparation Process of Equation-1

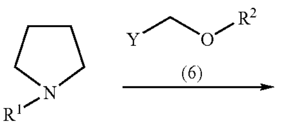

(5)

-continued

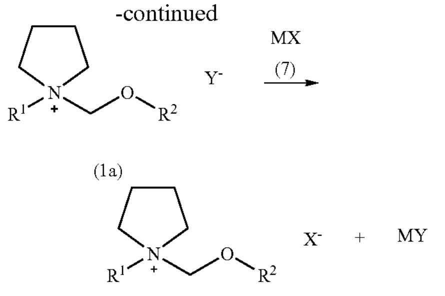

(1a)

(1)

An alkylpyrrolidine of the formula (5) wherein $R^1$ is the same as above is reacted with a compound of the formula (6) wherein $R^2$ is the same as above, and Y is Cl, Br, I or the like to prepare a quaternary ammonium salt of the formula (1a), which is then subjected to salt-exchange reaction with a compound of the formula (7) to prepare a quaternary ammonium salt of the formula (1). Represented by M in the formula (7) is one of atoms including hydrogen, alkali metal atoms such as Na, K and Li, alkaline-earth metal atoms such as Ca, Mg and Ba, and metal atoms such as Ag.

The tertiary amine of the formula (5) serving as the starting material and the compound of the formula (6) are both known substances.

Examples of tertiary amine of the formula (5) are methylpyrrolidine, ethylpyrrolidine, n-propylpyrrolidine, isopropylpyrrolidine, n-butylpyrrolidine, isobutylpyrrolidine, tert-butylpyrrolidine, etc.

Examples of compounds of the formula (6) are chloromethyl methyl ether, bromomethyl methyl ether, iodomethyl methyl ether, chloromethyl ethyl ether, bromomethyl ethyl ether, iodomethyl ethyl ether, chloromethyl n-propyl ether, bromomethyl n-propyl ether, iodomethyl n-propyl ether, chloromethyl iso-propyl ether, bromomethyl iso-propyl ether, iodomethyl iso-propyl ether, etc.

The tertiary amine of the formula (5) and the compound of the formula (6) are reacted in a suitable solvent.

The solvent to be used can be a wide variety of known solvents insofar as they are capable of solving the tertiary amine of the formula (5) and the compound of the formula (6) and will not adversely affect the reaction. Examples of such solvents are benzene, toluene, xylene and like aromatic hydrocarbons, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, diethyl ether, diisopropyl ether and like ethers, methyl acetate, ethyl acetate, butyl acetate and like esters, n-hexane, n-heptane and like aliphatic hydrocarbons, cyclohexane and like aliphatic hydrocarbons, etc. Preferable among these solvents are toluene and like aromatic hydrocarbons, chloroform and like hydrocarbon halides, acetone and like ketones and methyl acetate and like esters. These solvents can be used singly, or at least two of them are usable in admixture. Preferable to use are solvents which are free from water (up to 1000 ppm in water content).

The tertiary amine of the formula (5) and the compound of the formula (6) are used in the ratio usually of 0.5 to 5 moles, preferably 0.9 to 1.2 moles, of the latter per mole of the former.

The reaction is carried out usually at −30 to 100° C., more particularly at −10 to 40° C. The reaction is completed generally in several hours to about 24 hours.

The reaction of the quaternary ammonium salt of the formula (1a) obtained above with the compound of the formula (7) is carried out by a usual salt exchange reaction.

The compound of the formula (7) used as a starting material is a known compound. Examples of these are $CF_3COOH$, $CF_3COOLi$, $CF_3COOLi$, $CF_3COONa$, $CF_3COOK$, $CF_3COOAg$, $HCF_3SO_3BF_3$, $LiCF_3SO_3BF_3$, $NaCF_3SO_3BF_3$, $NaCF_3SO_3BF_3$, $AgCF_3SO_3BF_3$, $HClBF_3$, $LiClBF_3$, $NaClBF_3$, $KClBF_3$, $AgClBF_3$, $HAlF_4$, $LiAlF_4$, $NaAlF_4$, $KAlF_4$, $AgAlF_4$, $HN(SO_2F)_2$, $LiN(SO_2F)_2$, $NaN(SO_2F)_2$, $KN(SO_2F)_2$, $AgN(SO_2F)_2$, $HPF_6^-$, $LiPF_6^-$, $KPF_6^-$, $AgPF_6^-$, $HAsF_6$, $LiAsF_6$, $NaAsF_6$, $KAsF_6$, $AgAsF_6$, $HsbF_6$, $LiSbF_6$, $NaSbF_6$, $KSbF_6^-$, $LiAiF_4$, $NaAiF_4$, $AgSbF_6$, etc.

This salt exchange reaction is carried out in a suitable solvent. The solvent to be used can be a wide variety of known solvents insofar as they are capable of dissolving the quaternary ammonium salt of the formula (1a) and the compound of the formula (7) and will not adversely affect the reaction. Examples of such solvents are water, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, ethyl acetate, butyl acetate and like esters, dimethyl sulfoxide, dimethylformamide and like aprotic polar solvents. Preferable among these are methanol and like lower alcohols, chloroform and like hydrocarbon halides and water. These solvents are usable singly, or at least two of them are usable in admixture.

The quaternary ammonium salt of the formula (1a) and the compound of the formula (7) are used in the ratio usually of 0.3 to 5 moles, preferably 0.9 to 1.2 moles, of the latter per mole of the former.

The reaction proceeds usually rapidly, so that a solution of the two reactants as dissolved in a solvent is reacted at 5 to 150° C. for about 10 minutes to about 24 hours.

The desired products obtained by the foregoing respective reactions can each be readily isolated from the reaction mixture and purified by usual isolating and purifying means such as centrifuging, concentration, washing, organic solvent extraction, chromatography and recrystallization.

The salt exchange reaction can be carried out with use of an ion-exchange resin. Examples of the ion-exchange resin are anion-exchange resin. The salt exchange reaction is performed by exchanging anions in the resin into desired anions and then passing into the resin a solution dissolved therein the quaternary ammonium salt of the formula (1a). The solvent to be used can be a wide variety of known solvents insofar as they are capable of dissolving the salt of the formula (1a) and will not adversely affect the reaction. Examples of such solvents are water and alcohols.

In the case where the product is to be placed into use in which the presence of halogen in the product is objectionable, the amount of halogen present can be diminished by subjecting the halogen salt to neutralization or salt exchange, and further converting the product into a salt in conformity with the contemplated use. Examples of useful neutralizing agents are alkali metal salts, alkaline earth metal salts, organic alkali metal salts, silver salts, etc. More specific examples of such agents are sodium carbonate, potassium carbonate, lithium carbonate, calcium carbonate, sodium hydroxide, potassium hydroxide, lithium hydroxide, calcium hydroxide, sodium perchlorate, potassium perchlorate, lithium perchlorate, sodium acetate, potassium acetate, silver sulfate, silver nitrate, silver perchlorate, etc.

The reaction can be carried out in the same mode as the procedure for preparing the quaternary ammonium salt of the formula (1). The procedure for preparing the quaternary ammonium salt of the formula (1) is usable also as the subsequent procedure for converting the dehalogenated salt into a salt in conformity with the contemplated use.

The quaternary ammonium salt wherein X is $CF_3SO_3BF_3$ or $ClBF_3$ can be prepared by the following reaction.

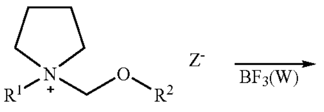

(8)

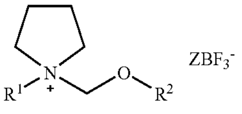

(9)

In the above, Z is $CF_3SO_3$ or Cl, W represents $H_2O$, methanol, diethyl ether, etc. (W) means nothing or $BF_3$ gas. $R^1$ and $R^2$ are the same as above.

This reaction is carried out in a suitable solvent. The solvent to be used can be a wide variety of known solvents insofar as they are capable of dissolving the quaternary ammonium salt of the formula (8) and the compound represented by the formula $BF_3(w)$ and will not adversely affect the reaction. Examples of such solvents are water, dichloromethane, chloroform, carbon tetrachloride and like hydrocarbon halides, methanol, ethanol, isopropanol, n-butanol, tert-butanol and like lower alcohols, acetone and like ketones, tetrahydrofuran, diethyl ether and like ethers. Preferable among these are methanol and like lower alcohols, chloroform and like hydrocarbon halides and water. These solvents are usable singly, or at least two of them are usable in admixture.

The quaternary ammonium salt of the formula (8) and the compound of the formula $BF_3(W)$ are used in the ratio usually of 0.3 to 5 moles, preferably 0.9 to 1.2 moles, of the latter per mole of the former. The reaction is conducted at about 0 to 150° C. for about 1 to 24 hours. It is possible to use $BF_3$ gas, so that the gas is directly added to a solution of the quaternary ammonium salt of the formula (8) in a suitable solvent. Further, $BF_3$ gas can be directly added to a solid or liquid quaternary ammonium salt without use of a solvent. The quaternary ammonium salt of the formula (8) and $BF_3$ gas are used in the ratio usually of 0.3 to 5 moles, preferably 0.9 to 1.2 moles, of the latter per mole of the former. The reaction is conducted at about −30 to 100° C. for about 1 to 24 hours.

The quaternary ammonium salt wherein X is $AlF_4$ can be prepared by the following reaction.

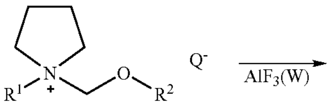

(10)

-continued

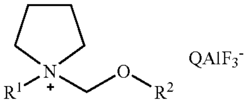

(11)

In the above, Q is F(HF)n ($0 \leqq n \leqq \infty$), W represents $H_2O$, etc. (W) means nothing or $H_2O$, etc. $R^1$ and $R^2$ are the same as above, n is preferably $0 \leqq n \leqq 20$, more preferably $0 \leqq n \leqq 10$.

This reaction is carried out in a suitable solvent. The solvent to be used can be a wide variety of known solvents insofar as they are capable of dissolving the quaternary ammonium salt of the formula (10) and the compound represented by the formula $AlF_3(W)$ and will not adversely affect the reaction. Examples of such solvents are water, dichloromethane, chloroform, carbon tetrachloride and like hydrocarbon halides, methanol, ethanol, isopropanol, n-butanol, tert-butanol and like lower alcohols, acetone and like ketones, tetrahydrofuran, diethyl ether and like ethers. These solvents are usable singly, or at least two of them are usable in admixture. The reaction is preferably conducted without use of a solvent.

The quaternary ammonium salt of the formula (10) and the compound of the formula $AlF_3(W)$ are used in the ratio usually of 0.3 to 5 moles, preferably 0.9 to 1.2 moles, more preferably one mole of the latter per mole of the former. The reaction is conducted at about 0 to 150° C. for about 1 to 24 hours. Thereafter, W can be removed by distillation in a vacuum or nitrogen-bubbling with heat to obtain a desired compound of the formula (11).

Stated specifically, the quaternary ammonium salt of the formula (1) wherein X is $AlF_4$ is prepared from a quaternary ammonium salt of the formula (1a) by the reaction procedure to be described below.

The quaternary ammonium salt of the formula (1a) is dissolved in excess amount of 50 to 100% hydrofluoric acid and the solution was heated at 0 to 100° C. for 1 to 24 hours to obtain the compound of the formula (10). To the compound (10) is added a specified amount of $AlF_3$ hydrate and the mixture was heated at 0 to 100° C. for 1 to 24 hours. Excess of hydrofluoric acid was removed from the resulting solution at 50 to 150° C. to obtain a desired compound of the formula (11).

Stated specifically, the quaternary ammonium salt of the formula (1) wherein X is $N(SO_2F)_2$ is prepared from a quaternary ammonium salt of the formula (1a) by the reaction procedure to be described below.

The quaternary ammonium salt of the formula (1a) is dissolved in water, and a specified amount of bisfluorosulfonimide acid or its alkali metal salt (lithium salt, sodium salt, potassium salt, etc.) is added to the solution. The solution was maintained at 0 to 25° C. for 30 minutes. The resulting desired compound was extracted with a suitable solvent (for example, dichloromethane, chloroform, ethyl acetate, etc.) and the extract was washed with water, concentrated in a vacuum and dried to obtain a desired compound of the formula (11).

Bisfluorosulfonimide acid is a known compound and can be prepared by a method disclosed, for example, in ROLF APPEL und GERHARD EISENHAUER, Chemische Berichte (1962), 95, 246-248.

Further, alkali metal salt of bisfluorosulfonimide acid can be prepared by a known method disclosed, for example, in P L DHINGRA, R L SINGHAL AND RAJENDAR D VERMA, Indian Journal of Chemistry (1985), 24A, 472-475.

Stated specifically, the quaternary ammonium salt of the formula (1) wherein X is $PF_6$ is prepared from a quaternary ammonium salt of the formula (1a) by the reaction procedure to be described below.

The quaternary ammonium salt of the formula (1a) is dissolved in dichloromethane, and a specified amount of an aqueous solution of sodium hexafluorophosphate is added to the solution to conduct the reaction at 5 to 150° C. for about 30 minutes. The resulting organic layer was extracted and the extract was repeatedly washed with water, concentrated in a vacuum and dried to isolate a desired compound.

Preparation Process of Equation-2

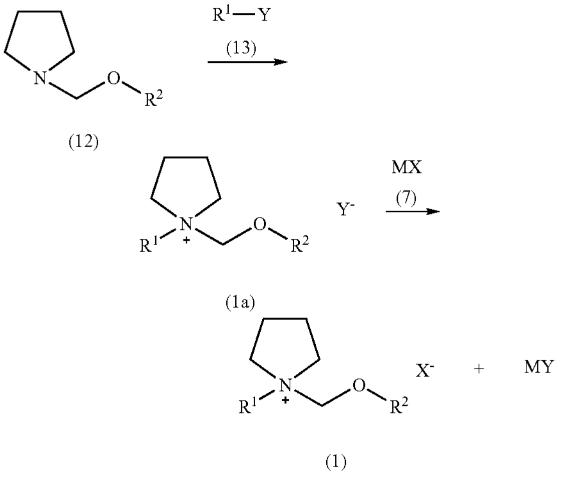

(12) (1a) (1)

An alkoxypyrrolidine of the formula (12) wherein $R^2$ is the same as above is reacted with a compound of the formula (13) wherein $R^1$ and Y are the same as above to prepare a quaternary ammonium salt of the formula (1a), which is then reacted with a compound of the formula (7) wherein M and X are the same as above to thereby prepare a quaternary ammonium salt of the formula (1) by salt exchange reaction. Represented by M in the formula (7) is one of atoms including hydrogen, alkali metal atoms such as Na, K and Li, alkaline-earth metal atoms such as Ca, Mg and Ba, and metal atoms such as Ag.

The alkoxypyrrolidine of the formula (12) serving as the starting material and the compound of the formula (13) are both known substances.

The alkoxypyrrolidine of the formula (12) is prepared by known processes. Such processes are disclosed, for example, in C. M. McLeod und G. M. Robinson, J. Chem. Soc. 119, 1470 (1921), G. M. Robinson und R. Robinson, J. Chem. Soc. 123, 532 (1923), Stewert, T. D.; Bradly, W. E., J. Am. Chem. Soc. 1932, 54, 4172-4183.

The alkoxypyrrolidine of the formula (12) is prepared generally by using pyrrolidine, formaldehyde or p-formaldehyde, alcohol, and alkali carbonate. Used per mole of pyrrolidine are 0.5 to 3.0 moles, preferably 0.6 to 1.5 moles of 10 to 38 wt % aqueous solution of formaldehyde or p-formaldehyde, 0.5 to 3.0 moles, preferably 2.0 to 3.0 moles of an alcohol, and 0.2 to 3.0 moles, preferably 0.4 to 1.0 mole of an alkali carbonate. The reaction is carried out at a temperature of −5 to 25° C. when aqueous solution of formaldehyde is used, and 60 to 100° C. when aqueous solution of p-formaldehyde is used, and is completed in several hours to about 24 hours. The alkoxypyrrolidine of the formula (12) can be readily isolated from the reaction mixture and purified by usual isolating means such as extraction and rectification.

Examples of the compound of the formula (13) are methyl chloride, methyl bromide, methyl iodide, ethyl chloride, ethyl iodide, ethyl bromide, n-propyl chloride, n-propyl bromide, n-propyl iodide, iso-propyl chloride, iso-propyl bromide, iso-propyl iodide, n-butyl chloride, n-butyl bromide, n-butyl iodide, iso-butyl chloride, iso-butyl bromide, iso-butyl iodide, tert-butyl chloride, tert-butyl bromide and tert-butyl iodide.

The alkoxypyrrolidine of the formula (12) is reacted with the compound of the formula (13) in a suitable solvent.

The solvent to be used can be a wide variety of those already known insofar as they are capable of dissolving the alkoxypyrrolidine of the formula (12) and the compound of the formula (13) and will not adversely affect the reaction. Examples of such solvents are benzene, toluene, xylene and like aromatic hydrocarbons, dichloromethane, chloroform, carbon tetrachloride and like hydrocarbon halides, methanol, ethanol, isopropanol, n-butanol, tert-butanol and like lower alcohols, acetone, methyl ethyl ketone and like ketones, diethyl ether, diisopropyl ether and like ethers, methyl acetate, ethyl acetate, butyl acetate and like esters, n-hexane, n-heptane and like aliphatic hydrocarbons, cyclohexane and like aliphatic hydrocarbons, etc. Preferable among these solvents are acetone and like ketone, toluene and like aromatic hydrocarbons, and chloroform and like hydrocarbon halides. These solvents can be used singly, or at least two of them are usable in admixture. Especially preferable to use are solvents which are free from water (up to 1000 ppm in water content).

The alkoxypyrrolidine of the formula (12) and the compound of the formula (13) are used in the ratio usually of 0.5 to 5 moles, preferably 0.9 to 1.2 moles, of the latter per mole of the former.

The reaction is carried out usually at 0 to 150° C. The reaction is completed generally in about 24 hours to about 72 hours. When an alkyl halide having a low boiling point is used for producing the quaternary salt, it is desirable to use an autoclave.

The reaction of the quaternary ammonium salt of the formula (1a) obtained above with the compound of the formula (7) is carried out by a usual salt exchange reaction. The details of the reaction are the same as in the process of Equation-1.

The quaternary ammonium salt of the formula (1a) contains water in an amount of preferably up to 100 ppm, more preferably up to 50 ppm, further more preferably up to 30 ppm, especially most preferably up to 10 ppm. When the quaternary ammonium salt of the formula (1) of the invention itself is a liquid at room temperature, the salt is usable as it is as an electrolytic solution. These salts are usable singly, or at least two of them are usable in admixture.

The quaternary ammonium salt of the formula (1) of the invention is usable as an electrolytic solution as mixed with a suitable organic solvent. Also the solvents are usable singly, or at least two of them are usable in admixture.

Examples of organic solvents are cyclic carbonic acid esters, chain carbonic acid esters, phosphoric acid esters, cyclic ethers, chain ethers, lactone compounds, chain esters, nitrile compounds, amide compounds, sulfone compounds, etc. These solvents may be used singly, or at least two of them are usable in admixture.

Although not limitative, the solvents given below are more specific examples of useful solvents.

Examples of cyclic carbonic acid esters are ethylene carbonate, propylene carbonate, butylene carbonate, etc. Preferable is propylene carbonate.

Examples of chain carbonic acid esters are dimethyl carbonate, ethylmethyl carbonate, methyl-n-propyl carbonate, methyl-isopropyl carbonate, n-butylmethyl carbonate, diethyl carbonate, ethyl-n-propyl carbonate, ethyl-iso-propyl carbonate, n-butylethyl carbonate, di-n-propyl carbonate, di-iso-propyl carbonate and di-n-butyl carbonate. Preferable are dimethyl carbonate and ethylmethyl carbonate.

Examples of phosphoric acid esters are trimethyl phosphate, triethyl phosphate, ethyldimethyl phosphate, diethylmethyl phosphate, etc.

Examples of cyclic ethers are tetrahydrofuran, 2-methyltetrahydrofuran, etc.

Examples of chain ethers are dimethoxyethane, etc.

Examples of lactone compounds are gamma-butyrolactone and the like.

Examples of chain esters are methyl propionate, methyl acetate, ethyl acetate, methyl formate, etc.

Examples of nitrile compounds are acetonitrile and the like.

Examples of amide compounds are dimethylformamide and the like.

Examples of sulfone compounds are sulfolane, methyl sulfolane, etc.

Preferable are cyclic carbonic acid esters, chain carbonic acid esters, nitrile compounds and sulfone compounds.

These solvents may be used singly, or at least two of them are usable in admixture.

Examples of mixtures of solvents are a mixture of cyclic carbonic acid ester and chain carbonic acid ester, a mixture of chain carbonic acid ester and chain carbonic acid ester and a mixture of sulfolane compound and sulfolane compound.

Examples of mixtures of cyclic carbonic acid ester and chain carbonic acid ester are ethylene carbonate and dimethyl carbonate; ethylene carbonate and ethylmethyl carbonate; ethylene carbonate and diethyl carbonate; propylene carbonate and dimethyl carbonate; propylene carbonate and ethylmethyl carbonate; propylene carbonate and diethyl carbonate; etc.

Examples of mixtures of chain carbonic acid ester and chain carbonic acid ester are dimethyl carbonate and ethylmethyl carbonate.

Examples of mixtures of sulfolane compound and sulfolane compound are sulfolane and methyl sulfolane.

Preferable examples of mixtures are ethylene carbonate and ethylmethyl carbonate; propylene carbonate and ethylmethyl carbonate; dimethyl carbonate and ethylmethyl carbonate; etc.

The quaternary ammonium salt of the formula (1) of the invention is usable as an electrolytic solution as mixed with chain carbonic acid ester which is an organic solvent. The solvents are usable singly, or at least two of them are usable in admixture.

Examples of chain carbonic acid esters are dimethyl carbonate, ethylmethyl carbonate, methyl-n-propyl carbonate, methyl-isopropyl carbonate, n-butylmethyl carbonate, diethyl carbonate, ethyl-n-propyl carbonate, ethyl-iso-propyl carbonate, n-butylethyl carbonate, di-n-propyl carbonate, di-iso-propyl carbonate and di-n-butyl carbonate. Preferable are dimethyl carbonate and ethylmethyl carbonate.

These solvents may be used singly, or at least two of them are usable in admixture.

Examples of mixtures of solvents are dimethyl carbonate and ethylmethyl carbonate.

When the electrolyte of the quaternary ammonium salt of the formula (1) of the invention is used as dissolved in an organic solvent, the concentration of the electrolyte is at least 0.1 M, preferably at least 0.5 M and more preferably at least 1 M.

The quaternary ammonium salt of the formula (1) of the invention or a solution of such a salt as dissolved in an organic solvent is usable as an electrolytic solution for electrochemical devices.

Examples of electrochemical devices are electric double-layer capacitors and secondary cells.

Electrolyte or electrolytic solution of the invention is usable as those used in known electrolytes or electrolytic solutions for electric double-layer capacitors or secondary cells.

When the electrolyte of the quaternary ammonium salt of the formula (1) of the invention is used as dissolved in an organic solvent for electrolytic solutions of electrochemical devices, the concentration of the electrolyte is at least 0.1 M, preferably at least 0.5 M and more preferably at least 1 M. If the concentration is lower than 0.1 M, the solution is low in electrical conductivity, providing electrochemical devices of impaired performance. The upper limit concentration is the concentration permitting the quaternary ammonium salt to separate from the organic solvent when the salt is liquid at room temperature. If the salt is free of separation, the upper limit concentration is 100%. When the quaternary ammonium salt is solid at room temperature, the concentration at which the organic solvent becomes saturated with the salt is the upper limit concentration.

An electrolytic solution for electrochemical devices can be prepared using the quaternary ammonium salt of the formula (1) of the invention. The electrolytic solution obtained by the invention is usable for electrochemical devices wherein electric energy can be stored by a physical activity or chemical activity and can be used suitably for example in electric double-layer capacitors and lithium cells.

A description will be given of a method of preparing an electrolytic solution for use in electric double-layer capacitors using the quaternary ammonium salt of the formula (1) of the invention. When the quaternary ammonium salt of the formula (1) of the invention itself is a liquid, the salt is usable as it is as an electrolytic solution, while the salt may be used as mixed with a suitable organic solvent. In preparing electrolytic solution for use in electric double-layer capacitors, since water adversely affects the performance of electric double-layer capacitors, it is desirable to conduct the work free from the atmospheric air, for example, within a glove box having an inert atmosphere of argon or nitrogen. The water content of the work environment can be controlled using a dewpoint meter and is preferably up to minus 60° C. When the work environment is in excess of minus 60° C. and if the work is carried out over a prolonged period of time, the electrolyte or electrolytic solution will absorb water from the atmosphere and therefore rises in water content. The water content of the electrolyte or electrolytic solution can be measured by a Karl Fischer moisture meter.

In the case where a solution of the quaternary ammonium salt of the formula (1) of the invention in an organic solvent is to be used as the electrolytic solution of electrochemical devices, the concentration of the electrolyte is preferably at least 0.1 M, more preferably at least 0.5 M, especially preferably at least 1 M. The upper limit concentration is not defined insofar as no precipitation or separation of the electrolyte occurs.

Examples of organic solvents to be used are various as previously mentioned, whereas since the properties such as dielectric constant, viscosity and melting point differ depending on the combination of the quaternary ammonium salt of the invention and the kind of solvent to be mixed therewith, it is desirable to determine the composition of the mixture in accordance with the combination of the quaternary ammonium salt of the formula (1) of the invention and the solvent to be mixed therewith for use.

For example, in the case of an electrolytic solution comprising N-methoxymethyl-N-methylpyrrolidinium trifluoromethane sulfonyltrifluoroborate and ethylmethyl carbonate, the solution comprises preferably 50 to 90 wt. %, more preferably 50 to 80 wt. % of the trifluoromethane sulfonyltrifluoroborate. In the case of an electrolytic solution comprising N-methoxymethyl-N-methylpyrrolidinium chlorotrifluoroborate and ethylmethyl carbonate, the solution comprises preferably 70 to 90 wt. %, more preferably 70 to 80 wt. % of the chlorotrifluoroborate. In the case of an electrolytic solution comprising N-methoxymethyl-N-methylpyrrolidinium tetrafluoroaluminate and ethylmethyl carbonate, the solution comprises preferably 50 to 90 wt. %, more preferably 50 to 80 wt. % of the tetrafluoroaluminate. In the case of an electrolytic solution comprising N-methoxymethyl-N-methylpyrrolidinium hexafluorophosphate and dimethyl carbonate, the solution comprises preferably 10 to 90 wt. %, more preferably 20 to 80 wt. %, further preferably 45 to 85 wt. % of the hexafluorophosphate. In the case of an electrolytic solution comprising N-methoxymethyl-N-methylpyrrolidinium hexafluorophosphate and ethylmethyl carbonate, the solution comprises preferably 40 to 90 wt. %, more preferably 40 to 80 wt. %, further preferably 40 to 60 wt. % of the hexafluorophosphate. In the case of an electrolytic solution comprising N-methoxymethyl-N-methylpyrrolidinium hexafluoroarsenate and ethylmethyl carbonate, the solution comprises preferably 30 to 90 wt. %, more preferably 40 to 80 wt. %, further preferably 40 to 60 wt. % of the hexafluoroarsenate. In the case of an electrolytic solution comprising N-methoxymethyl-N-methylpyrrolidinium hexafluoroantimonate and ethylmethyl carbonate, the solution comprises preferably 30 to 90 wt. %, more preferably 40 to 80 wt. % of the hexafluoroantimonate.

The quaternary ammonium salt of the formula (1) of the invention is usable as an electrolytic solution also for secondary cells, especially for lithium secondary cells. Since water adversely affects the characteristics of lithium cells as when the electrolytic solution of electric double-layer capacitors is prepared, the solution is prepared preferably within a glove box having its dewpoint controlled.

In the case where the quaternary ammonium salt of the formula (1) of the invention itself is a liquid, the salt is usable as an electrolytic solution when having a lithium salt dissolved therein. Alternatively, the quaternary ammonium salt of the formula (1) of the invention is admixed with a suitable organic solvent, and a lithium salt is dissolved in the mixture for use as an electrolytic solution. Examples of the lithium salts are lithium hexafluorophosphate lithium borofluoride, lithium perchlorate, lithium trifluoromethanesulfonate, lithium sulfonylimide and lithium sulfonylmethide. The lithium salt to be used can be a wide variety of salts and is not limited particularly insofar as the solution is free of separation of the salt.

The concentration of the lithium salt is usually 0.1 to 2.0 moles, preferably 0.15 to 1.5 moles, more preferably 0.2 to 1.2, especially preferably 0.3 to 1.0 moles. If the concentration is less than 0.1 mole and when the charge-discharge rate is great, depletion of lithium ion occurs in the vicinity of the electrode to result in impaired charge-discharge characteristics. If the lithium ion concentration is over 2.0 moles, the electrolytic solution has a high viscosity to entail lower electrical conductivity.

It is desired that anions forming the lithium salt includes $BF_4^-$. Although still remaining to be clarified, the reason appears to be that when the tetrafluoroborate is present, a passive film is formed over the surface of aluminum serving as a positive electrode current collector, inhibiting aluminum from dissolving out. It is desired to adjust the number of $BF_4^-$ anions present to at least 0.5%, preferably at least 0.8%, of the total number of anions in the electrolytic solution. The upper limit for the number of $BF_4^-$ anions to be contained is 100% of the total number of anions in the solution.

The quaternary ammonium salt is usable as an electrolytic solution as mixed with a suitable organic solvent. Also these salts are usable singly, or at least two of them are usable in admixture.

Examples of organic solvents are same as those stated above and are cyclic carbonic acid esters, chain carbonic acid esters, phosphoric acid esters, cyclic ethers, chain ethers, lactone compounds, chain esters, nitrile compounds, amide compounds, sulfone compounds, etc. These solvents may be used singly, or at least two of them are usable in admixture.

The quaternary ammonium salt of the formula (1) of the invention is usable as an electrolytic solution as mixed with chain carbonic acid ester which is an organic solvent. The solvents are usable singly, or at least two of them are usable in admixture.

Examples of chain carbonic acid esters are dimethyl carbonate, ethylmethyl carbonate, methyl-n-propyl carbonate, methyl-isopropyl carbonate, n-butylmethyl carbonate, diethyl carbonate, ethyl-n-propyl carbonate, ethyl-iso-propyl carbonate, n-butylethyl carbonate, di-n-propyl carbonate, di-iso-propyl carbonate and di-n-butyl carbonate. Preferable are dimethyl carbonate and ethylmethyl carbonate.

These solvents may be used singly, or at least two of them are usable in admixture.

Examples of mixtures of solvents are dimethyl carbonate and ethylmethyl carbonate.

It is desired that the electrolytic solution to be used in the present invention contain at least one of specific organic additives. Examples of specific organic additives are ethylene carbonate, vinylene carbonate, butylene carbonate, ethylene trithiocarbonate, vinylene trithiocarbonate and ethylene sulfite. Preferable are ethylene carbonate and vinylene carbonate. These additives may be used singly, or at lest two of them are usable in admixture. The organic additive incorporated into the solution forms on the surface of the negative electrode of the lithium cell a film known as SEI (solid electrolyte interface) for lithium ions to permeate therethrough selectively, inhibiting the decomposition of ammonium cations which form the quaternary ammonium salt or insertion of ammonium cations into the negative electrode material and consequently giving stabilized charge-discharge characteristics. Some kinds of such organic additives are substances also having the function of a diluting organic solvent.

The organic additive is used preferably in a proportion preferably of 1 to 40 wt. %, more preferably 1 to 30 wt. %, further more preferably 1 to 20 wt. %, most preferably 1 to 10 weight %, based on the weight of the entire electrolytic solution. If the proportion is less than 1 wt. %, a satisfactory film will not be formed over the surface of the negative electrode, permitting the decomposition of ammonium cations which form the quaternary ammonium salt or insertion of ammonium cations into the negative electrode material.

Electric double layer capacitors can be favorably fabricated using the electrolytic solution of the invention thus obtained. FIG. 1 shows an example of electric double layer capacitor. Electric double layer capacitors are not limited to those of coin shape as shown in FIG. 1. Such a capacitor may be in the form of an assembly of superposed electrodes as placed in a can, a roll of electrodes as wound up and placed in a can, or a so-called laminate as packaged in an aluminum laminate. A description will be given of the structure of the coin-shaped electric double layer capacitor as an example.

FIG. 1 is a diagram showing the coin-shaped electric double layer capacitor in section. Electrodes 1, 2 are arranged as opposed to each other with a separator interposed therebetween, and are housed in container members 4, 5. The electrode comprises a polarizable electrode portion made of a carbon material such as activated carbon, and a current collector portion. The container members 4, 5 need only to be free of corrosion with the electrolytic solution and are made, for example, from stainless steel, aluminum or the like. The container members 4, 5 are electrically insulated with an insulation gasket 6, which also hermetically seals off the interior of a metal container to prevent water and air from ingressing into the interior from outside the container. The current collector of the electrode 1 and the container member 4, as well as the current collector of the electrode 2 and a metal spacer 7, are held in contact with each other under suitable pressure by the presence of a metal spring 8, and are thereby electrically connected. To ensure enhanced electric conductivity, the current collector may be adhered with a carbon paste or like conductive paste.

The polarizable electrode is made preferably from a material having a great specific surface area and high electric conductivity. The material needs to be electrochemically stable to the electrolytic solution within the range of voltages to be applied for use. Examples of such materials are carbon materials, metal oxide materials, conductive high-molecular-weight materials, etc. In view of the cost, the material for the polarizable electrode is preferably carbon material.

Activated carbon materials are desirable as carbon materials. Examples of such materials are sawdust activated carbon, coconut shell activated carbon, pitch or coke activated carbon, phenolic resin activated carbon, polyacrylonitrile activated carbon, cellulosic activated carbon, etc.

Examples of metal oxide materials usable are ruthenium oxide, manganese oxide, cobalt oxide, etc.

Examples of conductive high-molecular-weight materials to be used are polyaniline, polypyrrole film, polythiophene film, poly(3,4-ethylenedioxythiophene) film, etc.

The electrode can be obtained by molding the polarizable electrode material and a binder by press work, or by admixing the polarizable electrode material with a binder and an organic solvent such as pyrrolidine to prepare a paste, coating aluminum foil or like current collector with the paste and drying the coated current collector.

Preferably, the separator has high electron insulating properties, is highly wettable with the electrolytic solution and highly permeable to ions, and needs to be electrochemically stable within the range of voltages to be applied. Although the material for the separator is not limited particularly, it is suitable to use paper made from rayon, Manila hemp or the like, porous polyolefin film, nonwoven polyethylene fabric, nonwoven polypropylene fabric, etc.

The electrolytic solution according to the invention and thus prepared is suitable for use in fabricating lithium secondary cells. The lithium secondary cell of the invention is, for example, in the form of a coin, hollow cylinder, square or rectangle or laminate. FIG. 2 shows a coin-shaped cell as an example of lithium secondary cell.

The lithium secondary cell will be described below based on FIG. 2.

Into internal space defined by a positive electrode can 14 and a negative electrode can 15 are placed a positive electrode 11, separator 13, negative electrode 12 and spacer 17 in this order to provide a stack of superposed layers as positioned on the positive electrode can 14. A spring 18 is interposed between the negative electrode can 15 and the spacer 17 to press the positive electrode 11 and the negative electrode 12 against each other and fixedly position the electrodes in place. The assembly of positive electrode 11, separator 13 and negative electrode 12 is impregnated with the electrolytic solution. With a gasket 16 provided between the positive and negative cans 14, 15, the two cans 14 and 15 are joined by crimping, whereby the stack of components is enclosed as sealed off.

Examples of positive electrode active substances are composite oxides of lithium and transition metal or metals, such as $LiCoO_2$, $LiNiO_2$, $LiNi_{1-x}Co_xO_2$, $LiNi_{1-y-z}Co_yMn_zO_2$, $LiNi_{0.5}Mn_{0.5}O_2$, $LiMnO_2$, $LiMn_2O_4$ and $LiNi_{0.5}Mn_{1.5}O_4$, oxides such as $TiO_2$ and $V_2O_5$, sulfides such as $TiS_2$ and FeS, etc. From the viewpoint of cell capacity and energy density, composite oxides of lithium and transition metal or metals are desirable.

In the above, $1>x>0$, $1>y>0$, $1>z>0$, $y+z<1$. Such a positive electrode active substance can be molded into a positive electrode along with known auxiliary conductive agent and binder under pressure. Alternatively, the positive electrode can be made by mixing the positive electrode active substance with pyrrolidine or like organic solvent along with known conductive agent and binder to prepare a paste, coating a current collector of aluminum foil with the paste and drying the coating.

Examples of negative electrode active substances are a metal lithium, alloy of metal lithium and other metal, and a material for lithium ions to be inserted thereinto and to be released therefrom. Examples of alloys of metal lithium and other metals are Li—Al, Li—Sn, Li—Zn, Li—Si, etc. Examples of materials for lithium ions to be inserted thereinto and to be released therefrom are carbon materials prepared by firing a resin or pitch, a carbon material obtained by adding a boron compound to such a carbon material, natural graphite, etc. These negative electrode materials can be used singly, or at least two of them are usable in admixture.

Such a negative electrode material can be molded into a negative electrode along with known auxiliary conductive agent and binder under pressure. Alternatively, the negative electrode can be made by mixing the negative electrode active substance with pyrrolidone or like organic solvent along with known conductive agent and binder to prepare a paste, coating a current collector of copper foil with the paste and drying the coating.

The separator for use in the invention can be made from a material which is not limited particularly insofar as the material readily passes the electrolytic solution therethrough, has insulating properties and is chemically stable.

The quaternary ammonium salt of the formula (1) of the invention and the electrolytic solution containing the salt are high in electrical conductivity and solubility in organic solvents, and are suitable for use as an electrolytic solution for electrochemical devices. Examples of electrochemical devices are electric double-layer capacitors, secondary cells, solar cells of the pigment sensitizer type, electrochromic devices, condenser, etc., which are nevertheless not limitative. Especially suitable as electrochemical devices are electric double-layer capacitors and secondary cells.

Figure 1:
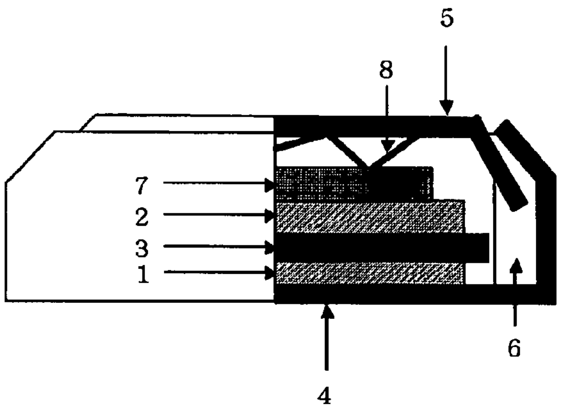
FIG. 1 is a sectional view showing an electric double-layer capacitor.

1 electrode, 2 electrode, 3 separator, 4 container member, 5 container member, 6 gasket, 7 spacer, 8 spring, 11 positive electrode, 12 negative electrode, 13 separator, 14 positive electrode can, 15 negative electrode can, 16 gasket, 17 spacer, 18 spring, 19 cylindrical glass container, 20 cylindrical screw cap, 21 electrode roll, 22 electric lead, 23 electric lead, 24 core, 25 positive electrode sheet, 26 negative electrode sheet, 27 separator, 28 separator

BEST MODE OF CARRYING OUT THE INVENTION

The present invention will be described with reference to the following Examples, but is not limited to these examples. Organic solvents used such as propylene carbonate, dimethyl carbonate, ethylmethyl carbonate, ethylene carbonate, etc. are products of Kishida Chemical Co., Ltd., lithium battery grade. Water content was measured by a Karl Fischer moisture meter (Hiranuma Moisture Meter AQ-7, product of Hiranuma Sangyo Co., Ltd.).

Preparation Example 1

Preparation of N-methoxymethyl-N-methylpyrrolidinium chloride

A 50.0 g quantity of N-methylpyrrolidine (reagent, product of Tokyo Kasei Co., Ltd., purified by rectification, up to 0.1 wt. % of both of pyrrolidine and water) was dissolved in 292.0 g of dehydrated acetone (up to 0.1 wt. % of water content), followed by replacement with nitrogen. Chloromethyl methyl ether (47.3 g, reagent, product of Tokyo Kasei Co., Ltd., purified by distillation) was added dropwise to the solution at 5° C. over a period of 1 hour. The mixture was stirred at 5 to 15° C. for 4 hours to complete the reaction. The reaction mixture was filtered, and the resulting solid product was washed with 120 g of acetone. The washed product was dried in a vacuum to obtain 92.5 g of the desired product (white solid).

$^1$H-NMR ($CD_3OD$) δ ppm:

2.22 (m 4H), 3.11 (s 3H), 3.46 (m 2H), 3.60 (m 2H), 3.67 (s 3H), 4.65 (s 2H)

Preparation Example 2

Preparation of N-ethyl-N-methoxymethylpyrrolidinium chloride

A 34.71 g quantity of N-ethylpyrrolidine (reagent, product of Tokyo Kasei Co., Ltd., purified by rectification, up to 0.1 wt. % of both of pyrrolidine and water) was dissolved in 189 g of dehydrated acetone (up to 0.1 wt. % of water content), followed by replacement with nitrogen. Chloromethyl ethyl ether (28.18 g) was added dropwise to the solution at 5° C. over a period of 1 hour. The mixture was stirred at 5° C. for 5 hours to complete the reaction. The reaction mixture was filtered, and the resulting solid product was washed with 100 g of acetone. The washed product was dried in a vacuum to obtain 50.08 g of white solid.

$^1$H-NMR ($CD_3OD$) δ ppm:

1.36 (m 3H), 2.17 (m 4H), 3.41-3.64 (m 6H), 3.64 (s 3H), 4.59 (s 2H)

Preparation Example 3

Preparation of N-ethoxymethyl-N-methylpyrrolidinium chloride

A 87.0 g quantity of N-methylpyrrolidine (reagent, product of Tokyo Kasei Co., Ltd., purified by rectification, up to 0.1 wt. % of both of pyrrolidine and water) was dissolved in 510 g of dehydrated acetone (up to 0.1 wt. % of water content), followed by replacement with nitrogen. Chloromethyl ethyl ether (96.6 g) was added dropwise to the solution at 3° C. over a period of 1 hour. The mixture was stirred at 5 to 15° C. for 4 hours to complete the reaction. The reaction mixture was concentrated and dried in a vacuum at reduced pressure. To the resulting product was added 700 ml of a solvent mixture of 2-butanone/acetone (8/2=V/V) and recrystallized at −30° C. The precipitate was filtered, and the resulting solid product was washed with a solvent mixture of 2-butanone/acetone. The washed product was dried in a vacuum to obtain 183.4 g of the desired product (white crystal).

$^1$H-NMR ($CDCl_3$) δ ppm:

1.30 (t 3H), 2.23 (m 4H), 3.12 (s 3H), 3.47 (m 2H), 3.60 (m 2H), 3.89 (q 2H), 4.71 (s 2H)

Example 1

Preparation of N-methoxymethyl-N-methylpyrrolidinium trifluoroacetate

In 100 g of methanol dissolved 14.94 g of sodium trifluoroacetate. To the solution was added 18.20 g of N-methoxymethyl-N-methylpyrrolidinium chloride and the mixture was stirred for 1 hour, concentrated in a vacuum and dried with use of a vacuum pump. The resulting product was dissolved in 500 ml of dichloromethane and the mixture was filtered with membrane filter, concentrated in a vacuum and dried in a vacuum to obtain 26.52 g of the desired product (colorless liquid). The product was checked for $^1$H-NMR, electrical conductivity and voltage resistance.

The electrical conductivity was measured using an electrical conductivity meter (product of Radiometer Analytical SAS). The measuring cell used was CDC641T, product of Radiometer Analytical SAS.

The voltage resistance was measured using a 3-pole electrochemical cell. Used as the working electrode was a glassy carbon electrode (product of BAS Inc.) 1.0 mm in diameter and 0.0079 $cm^{-2}$ in electrode area. The reference electrode used was a silver wire (product of the Nilaco Corp., 99.99% in purity) having a diameter of 0.5 mm. The counter electrode used was a platinum electrode (product of BAS Inc. 11-2233) measuring 0.5 mm in diameter and 50 mm in length. Linear sweep voltammetry was carried out to individually determine the potentials giving an oxidizing current density and reducing current density of 0.5 $mAcm^{-2}$. The difference between the potentials was taken as the voltage resistance. The potential sweep application speed was 50 $mVs^{-1}$. HZ-3000, product of Hokuto Denko Co., Ltd. was used for electrochemical measurement.

$^1$H-NMR ($CD_3OD$) δ ppm:

2.20 (m 4H), 3.09 (s 3H), 3.43 (m 2H), 3.57 (m 2H), 3.65 (s 3H), 4.59 (s 2H)

electrical conductivity: 7.14 mS/cm (25° C.)

Example 2

Preparation of N-methoxymethyl-N-methylpyrrolidinium trifluoromethanesulfonate

In 116 g of dehydrated chloroform (reagent, Wako Pure Chemical Ind. Ltd.) was dissolved 24.3 g of N-methoxymethyl-N-methylpyrrolidinium chloride. To the solution was added dropwise 24.3 g of trifluoromethane sulfonic acid (reagent, Aldrich Corp.) at 5° C. over a period of 1 hour. The mixture was reacted at room temperature for 2 hours with gradual increase of temperature. The reaction mixture was concentrated and dried in a vacuum. The residue was purified through alumina column (ICN Biomedicals. GmbH, ICN Alumina N, Act.1/eluent acetonitrile). The eluate was concentrated and dried in a vacuum to obtain 39.1 g of the desired product (colorless liquid).

$^1$H-NMR ($CD_3OD$) δ ppm:

2.20 (m 4H), 3.09 (s 3H), 3.45 (m 2H), 3.57 (m 2H), 3.66 (s 3H), 4.59 (s 2H)

electrical conductivity: 4.9 mS/cm (25° C.)

voltage resistance: 5.7V

Example 3

Preparation of N-methoxymethyl-N-methylpyrrolidinium trifluoromethane sulfonyltrifluoroborate In 51.2 g of dehydrated methanol (reagent, Kanto Chemical Co., Inc.) was dissolved 38.7 g of N-methoxymethyl-N-methylpyrrolidinium trifluoromethanesulfonate prepared in Example 2 and thereto was added dropwise 17.3 g of borontrifluoride-methanol complex (reagent, product of Tokyo Kasei Co., Ltd., purified by distillation) over a period of 0.5 hour. The mixture was reacted at room temperature for 1 hour and for 3 hours 50° C. with gradual increase of temperature. After removing methanol at ordinary pressure, excess of borontrifluoride-methanol complex was removed in a vacuum. The residue was purified through alumina column (ICN Biomedicals. GmbH, ICN Alumina N, Act.1/eluent acetonitrile). The eluate was concentrated and dried in a vacuum to obtain 43.3 g of the desired product (colorless liquid). The product was checked for $^1$H-NMR, $^{19}$F-NMR, electrical conductivity and voltage resistance as in Example 1.

$^1$H-NMR ($CD_3OD$) δ ppm:

2.20 (m 4H), 3.09 (s 3H), 3.45 (m 2H), 3.61 (m 2H), 3.66 (s 3H), 4.59 (s 2H)

$^{19}$F-NMR ($CD_3OD$) δ ppm: −79.12, −150.68 electrical conductivity: 5.26 mS/cm (25° C.)

voltage resistance: 6.1V

Example 4

Preparation of N-methoxymethyl-N-methylpyrrolidinium chlorotrifluoroborate

In 50.0 g of methanol was dissolved 50.0 g of N-methoxymethyl-N-methylpyrrolidinium chloride and thereto was added 110.14 g of methanol solution of 30% $HClBF_3$. $N_2$ was bubbled through the mixture with heating at 130° C. to remove methanol, hydrogen chloride and an excess of $HClBF_3$ and obtain 70.11 g of the desired product (brown liquid). The product was checked for $^1$H-NMR, electrical conductivity and voltage resistance as in Example 1.

$^1$H-NMR ($CD_3OD$) δ ppm:

2.21 (m 4H), 3.10 (s 3H), 3.47 (m 2H), 3.57 (m 2H), 3.66 (s 3H), 4.62 (s 2H)

electrical conductivity: 7.9 mS/cm (25° C.)

voltage resistance: 6.3V

Example 5

Preparation of N-methoxymethyl-N-methylpyrrolidinium tetrafluoroaluminate

N-methoxymethyl-N-methylpyrrolidinium chloride (50.0 g) was mixed with a solution of hydrofluoric acid. $N_2$ was bubbled through the mixture with heating at 60° C. to remove hydrogen chloride and an excess of hydrofluoric acid and obtain 59.52 g of N-methoxymethyl-N-methylpyrrolidinium fluoride. In 1000 g of 50% aqueous solution of hydrofluoric acid was dissolved 156 g of aluminum hydroxide at room temperature and the mixture was filtered. The filtrate was cooled to obtain 442.76 g of aluminum fluoride nonahydrates. To 30.4 g of the above N-methoxymethyl-N-methylpyrrolidinium fluoride was added 36.4 g of aluminum fluoride nonahydrates at 50° C. with stirring. $N_2$ was bubbled through the mixture with heating at 130° C. to remove hydrofluoric acid and obtain 29.4 g of the desired product (brown liquid). The product was checked for $^1$H-NMR, electrical conductivity and voltage resistance as in Example 1.

$^1$H-NMR ($CD_3OD$) δ ppm:

2.20 (m 4H), 3.10 (s 3H), 3.45 (m 2H), 3.60 (m 2H), 3.66 (s 3H), 4.63 (s 2H)

electrical conductivity: 7.1 mS/cm (25° C.)

voltage resistance: 6.3V

Example 6

Preparation of N-methoxymethyl-N-methylpyrrolidinium pentafluoroethyl trifluoroborate In 25.0 g of methanol was dissolved 25.0 g of N-methoxymethyl-N-methylpyrrolidinium chloride prepared in Preparation Example 1 and thereto was added 99.20 g of a solution of 30 wt. % of $H(C_2F_5BF_3)$ [Journal of Fluorine Chemistry 123 (2003) 127-131] in methanol. $N_2$ was bubbled through the mixture with heating at 130° C. to remove hydrogen chloride, an excess of $H(C_2F_5BF_3)$ and methanol and obtain 47.5 g of the desired product. The product was checked for $^1$H-NMR and electrical conductivity as in Example 1.

$^1$H-NMR ($CD_3OD$) δ ppm:

2.19 (m 4H), 3.07 (s 3H), 3.43 (m 2H), 3.56 (m 2H), 3.65 (s 3H), 4.59 (s 2H)

electrical conductivity: 6.7 mS/cm (25° C.)

Example 7

Preparation of N-methoxymethyl-N-methylpyrrolidinium bis(fluorosulfonyl)imide

In 11.5 g of water was dissolved 11.3 g of N-methyl-N-methoxymethylpyrrolidinium chloride and thereto was added a solution of 15.0 g of potassium bis(fluorosulfonyl)imide in 15.6 g of water at room temperature. The mixture was stirred for 30 minutes, and dichloromethane was added to the mixture for extraction. The organic layer was washed with 4.0 g of water 13 times, thereafter concentrated in a vacuum and dried, giving 16.9 g of the desired product in the form of a pale-yellow liquid. The product was checked for $^1$H-NMR and electrical conductivity as in Example 1.

$^1$H-NMR ($CD_3OD$) δ ppm:

2.22 (m 4H), 3.09 (s 3H), 3.43 (m 2H), 3.59 (m 2H), 3.66 (s 3H), 4.58 (s 2H)

electrical conductivity: 10.3 mS/cm (25° C.)

Example 8

Preparation of N-methoxymethyl-N-methylpyrrolidinium hexafluorophosphate

In 120 g of water was dissolved 20.0 g of N-methoxymethyl-N-methylpyrrolidinium chloride and thereto was added 20.3 g of sodium hexafluorophosphate to obtain a white solid. The mixture was stirred for 30 minutes, and dichloromethane was added to the mixture for extraction. The extract was washed with 20 g of water 15 times, thereafter dried, giving 23.3 g of the desired product in the form of a white solid.

$^1$H-NMR ($CD_3OD$) δ ppm:

2.19 (m 4H), 3.07 (s 3H), 3.43 (m 2H), 3.55 (m 2H), 3.65 (s 3H), 4.56 (s 2H)

Example 9

Preparation of N-methoxymethyl-N-methylpyrrolidinium hexafluoroarsenate

In 50.0 g of water was dissolved 25.1 g of N-methoxymethyl-N-methylpyrrolidinium chloride and thereto was added 30.0 g of lithium hexafluoroarsenate (reagent, Aldrich Corp.). The mixture was reacted at room temperature for 1 hour, and 79.2 g of dichloromethane was added to the mixture for extraction. The extract was washed with 100 ml of water 15 times, thereafter concentrated and dried in a vacuum, giving 32.4 g of the desired product in the form of a white solid.

$^1$H-NMR ($CD_3OD$) δ ppm:

2.20 (m 4H), 3.08 (s 3H), 3.44 (m 2H), 3.56 (m 2H), 3.65 (s 3H), 4.57 (s 2H)

Example 10

Preparation of N-methoxymethyl-N-methylpyrrolidinium hexafluoroantimonate

In 100 g of methanol was dissolved 12.1 g of N-methoxymethyl-N-methylpyrrolidinium chloride and thereto was added 24.97 g of silver hexafluoroantimonate (reagent, Aldrich Corp.). The mixture was reacted at 5° C. for 1 hour, and the resulting silver chloride was filtered. The filtrate was concentrated and 300 g of dichloromethane and 100 g of water were added to the concentrate for extraction. The extract was washed with 100 ml of water 15 times, thereafter concentrated and dried in a vacuum, giving 25.5 g of the desired product in the form of a white solid.

$^1$H-NMR ($CD_3OD$) δ ppm:

2.20 (m 4H), 3.07 (s 3H), 3.43 (m 2H), 3.56 (m 2H), 3.65 (s 3H), 4.56 (s 2H)

Example 11

Preparation of N-ethyl-N-methoxymethylpyrrolidinium chlorotrifluoroborate

In 35.0 g of methanol was dissolved 35.0 g of N-ethyl-N-methoxymethylpyrrolidinium chloride and thereto was added 71.08 g of methanol solution of 30% $HClBF_3$. $N_2$ was bubbled through the mixture with heating at 130° C. to remove methanol, hydrogen chloride and an excess of $HClBF_3$ and obtain 43.49 g of the desired product (brown liquid). The product was checked for $^1$H-NMR and electrical conductivity as in Example 1.

$^1$H-NMR ($CD_3OD$) δ ppm:

1.35 (m 3H), 2.19 (m 4H), 3.43-3.68 (m 6H), 3.64 (s 3H), 4.57 (s 2H)

electrical conductivity: 6.0 mS/cm (25° C.)

Example 12

Preparation of N-ethyl-N-methoxymethylpyrrolidinium tetrafluoroaluminate

N-ethyl-N-methoxymethylpyrrolidinium chloride (44.3 g) was mixed with a solution of hydrofluoric acid. $N_2$ was bubbled through the mixture with heating at 60° C. to remove hydrogen chloride and an excess of hydrofluoric acid and obtain 62.10 g of N-ethyl-N-methoxymethylpyrrolidinium fluoride. In 1000 g of 50% aqueous solution of hydrofluoric acid was dissolved 156 g of aluminum hydroxide at room temperature and the mixture was filtered. The filtrate was cooled to obtain 442.76 g of aluminum fluoride nonahydrates. To 46.00 g of the above N-ethyl-N-methoxymethylpyrrolidinium fluoride was added 53.04 g of aluminum fluoride nonahydrates at 50° C. with stirring. $N_2$ was bubbled through the mixture with heating at 130° C. to remove hydrofluoric acid and obtain 45.5 g of the desired product (brown liquid). The product was checked for $^1$H-NMR and electrical conductivity as in Example 1.

$^1$H-NMR ($CD_3OD$) δ ppm:

1.36 (m 3H), 2.20 (m 4H), 3.47-3.65 (m 6H), 3.66 (s 3H), 4.64 (s 2H)

electrical conductivity: 7.3 mS/cm (25° C.)

Example 13

Preparation of N-Ethyl-N-methoxymethylpyrrolidinium hexafluorophosphate

In 70.00 g of water was dissolved 35.00 g of N-ethyl-N-methoxymethylpyrrolidinium chloride and thereto was added 32.70 g of sodium hexafluorophosphate to obtain a white solid. The mixture was stirred for 30 minutes, and chloroform was added to the mixture for extraction. The extract was washed with 50 g of water 15 times, thereafter dried, giving 32.60 g of the desired product in the form of a white solid. The product was checked for $^1$H-NMR as in Example 1.

$^1$H-NMR ($CD_3OD$) δ ppm:

1.35 (m 3H), 2.19 (m 4H), 3.42-3.59 (m 6H), 3.64 (s 3H), 4.54 (s 2H)

Example 14

Preparation of N-ethyl-N-methoxymethylpyrrolidinium hexafluoroarsenate

In 40.0 g of water was dissolved 13.12 g of N-ethyl-N-methoxymethylpyrrolidinium chloride and thereto was added 14.30 g of lithium hexafluoroarsenate (reagent, Wako Pure Chemical Ind. Ltd.). The mixture was reacted at room temperature for 1 hour, and 30.00 g of chloroform was added to the mixture for extraction. The extract was washed with 15.0 g of water 15 times, and thereafter dried, giving 11.50 g of the desired product in the form of a white solid. The product was checked for $^1$H-NMR as in Example 1.

$^1$H-NMR ($CD_3OD$) δ ppm:

1.35 (m 3H), 2.19 (m 4H), 3.42-3.59 (m 6H), 3.64 (s 3H), 4.53 (s 2H)

Example 15

Preparation of N-ethoxymethyl-N-methylpyrrolidinium chlorotrifluoroborate

In 35.0 g of methanol was dissolved 35.0 g of N-ethoxymethyl-N-methylpyrrolidinium chloride and thereto was added 71.08 g of methanol solution of 30% $HClBF_3$. $N_2$ was bubbled through the mixture with heating at 130° C. to remove methanol, hydrogen chloride and an excess of $HClBF_3$ and obtain 41.11 g of the desired product (brown liquid). The product was checked for $^1$H-NMR and electrical conductivity as in Example 1.

$^1$H-NMR ($CD_3OD$) δ ppm:

1.30 (t 3H), 2.22 (m 4H), 3.10 (s 3H), 3.44 (m 2H), 3.61 (m 2H), 3.90 (q 2H), 4.67 (s 2H)

electrical conductivity: 5.3 mS/cm (25° C.)

Example 16

Preparation of N-ethoxymethyl-N-methylpyrrolidinium tetrafluoroaluminate

N-ethoxymethyl-N-methylpyrrolidinium chloride (60.90 g) was mixed with a solution of hydrofluoric acid. $N_2$ was bubbled through the mixture with heating at 60° C. to remove hydrogen chloride and an excess of hydrofluoric acid and obtain 62.10 g of N-ethoxymethyl-N-methylpyrrolidinium fluoride. In 1000 g of 50% aqueous solution of hydrofluoric acid was dissolved 156 g of aluminum hydroxide at room temperature and the mixture was filtered. The filtrate was cooled to obtain 442.76 g of aluminum fluoride nonahydrates. To 46.70 g of the above N-ethoxymethyl-N-methylpyrrolidinium fluoride was added 53.40 g of aluminum fluoride nonahydrates at 50° C. with stirring. $N_2$ was bubbled through the mixture with heating at 130° C. to remove hydrofluoric acid and obtain 46.80 g of the desired product (brown liquid). The product was checked for $^1$H-NMR and electrical conductivity as in Example 1.

$^1$H-NMR ($CD_3OD$) δ ppm:

1.30 (t 3H), 2.23 (m 4H), 3.15 (s 3H), 3.50 (m 2H), 3.65 (m 2H), 3.92 (q 2H), 4.74 (s 2H)

electrical conductivity: 7.7 mS/cm (25° C.)

Example 17

Preparation of N-ethoxymethyl-N-methylpyrrolidinium hexafluorophosphate

In 70.00 g of water was dissolved 35.00 g of N-ethoxymethyl-N-methylpyrrolidinium chloride and thereto was added 32.70 g of sodium hexafluorophosphate to obtain a white solid. The mixture was stirred for 30 minutes, and chloroform was added to the mixture for extraction. The extract was washed with 50 g of water 15 times, thereafter dried, giving 37.50 g of the desired product in the form of a white solid. The product was checked for $^1$H-NMR as in Example 1.

$^1$H-NMR ($CD_3OD$) δ ppm:

1.30 (t 3H), 2.23 (m 4H), 3.08 (s 3H), 3.42 (m 2H), 3.59 (m 2H), 3.89 (q 2H), 4.62 (s 2H)

Example 18

Preparation of N-ethoxymethyl-N-methylpyrrolidinium hexafluoroarsenate

In 40.0 g of water was dissolved 13.12 g of N-ethoxymethyl-N-methylpyrrolidinium chloride and thereto was added 14.30 g of lithium hexafluoroarsenate (reagent, Wako Pure Chemical Ind. Ltd.). The mixture was reacted at room temperature for 1 hour, and 30.00 g of chloroform was added to the mixture for extraction. The extract was washed with 15.0 g ml of water 15 times, and thereafter dried, giving 11.70 g of the desired product in the form of a white solid. The product was checked for $^1$H-NMR as in Example 1.

$^1$H-NMR ($CD_3OD$) δ ppm:

1.31 (t 3H), 2.22 (m 4H), 3.09 (s 3H), 3.42 (m 2H), 3.59 (m 2H), 3.88 (q 2H), 4.62 (s 2H)

Example 19

The N-methoxymethyl-N-methylpyrrolidinium trifluoroacetate prepared in Example 1 and propylene carbonate were mixed together within a dry box having a nitrogen atmosphere, up to −60° C. in dew point, to obtain solutions having varying concentrations. The solutions prepared were checked for water content by a Karl Fischer moisture meter and found to be up to 30 ppm in water content. Table 1 shows the concentrations of the solutions. The solutions were checked for electrical conductivity.

<Observation of State of Compositions>

The above compositions were each placed into glass containers having a screw plug inside the dry box, in an amount of 4 cc in each container and brought out of the dry box. The glass containers containing the composition were immersed in a constant-temperature bath and held at 25° C., 0° C. or −30° C. for 5 hours and checked for state visually. The results are shown in Tables, in which "-" indicates separation into two layers, and "solid" represents a solid state.

<Measurement of Electrical Conductivity>

The solution compositions which were found to be in a liquid state free of separation or solidification were brought out of the dry box and checked for electrical conductivity using a conductivity meter (CDM210, product of Radiometer Analytical SAS). The measuring cell used was XE-100 (product of Radiometer Analytical SAS).

TABLE 1

| | electrolyte (wt %) | PC (wt %) | electrical conductivity (25° C.) (mS/cm) | (0° C.) (mS/cm) | (−30° C.) (mS/cm) |
|---|---|---|---|---|---|
| Ex. 19 | 20 | 80 | 9.9 | 5.9 | 2.0 |
| | 30 | 70 | 12.0 | 6.7 | 2.2 |
| | 40 | 60 | 12.9 | 6.9 | 2.2 |
| | 60 | 40 | 12.6 | 6.4 | 1.8 |
| | 80 | 20 | 10.4 | 4.8 | solid |
| | 100 | 0 | 7.1 | 3.1 | solid |

Example 20

The N-methoxymethyl-N-methylpyrrolidinium trifluoromethane sulfonyltrifluoroborate prepared in Example 3 and propylene carbonate were mixed together within a dry box having a nitrogen atmosphere, up to −60° C. in dew point, to obtain solutions having varying concentrations. The solutions prepared were checked for water content by a Karl Fischer moisture meter and found to be up to 30 ppm in water content. Table 2 shows the concentrations of the solutions. The solutions were checked for electrical conductivity in the same manner as in Example 19.

TABLE 2

| | electrolyte (wt %) | PC (wt %) | electrical conductivity (25° C.) (mS/cm) | (0° C.) (mS/cm) | (−30° C.) (mS/cm) |
|---|---|---|---|---|---|
| Ex. 20 | 20 | 80 | 11.0 | 6.5 | 2.2 |
| | 30 | 70 | 13.0 | 7.5 | 2.5 |
| | 40 | 60 | 13.6 | 7.7 | 2.4 |
| | 60 | 40 | 12.1 | 6.3 | 1.5 |
| | 80 | 20 | 9.0 | 4.2 | 0.8 |
| | 100 | 0 | 5.3 | 2.1 | solid |

Example 21

The N-methoxymethyl-N-methylpyrrolidinium trifluoromethane sulfonyltrifluoroborate prepared in Example 3 and ethylmethyl carbonate were mixed together within a dry box having a nitrogen atmosphere, up to −60° C. in dew point, to obtain solutions having varying concentrations. The solutions prepared were checked for water content by a Karl Fischer moisture meter and found to be up to 30 ppm in water content. Table 3 shows the concentrations of the solutions. The solutions were checked for electrical conductivity in the same manner as in Example 19.

TABLE 3

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 21 | 20 | 80 | — | — | — |
| | 40 | 60 | — | — | — |
| | 50 | 50 | 12.6 | 8.0 | 3.2 |
| | 60 | 40 | 11.3 | 6.8 | 2.7 |
| | 80 | 20 | 10.1 | 4.9 | 1.6 |
| | 100 | 0 | 5.3 | 2.1 | solid |

Example 22

The solutions were checked for electrical conductivity in the same manner as in Example 19 with the exception of using N-methoxymethyl-N-methylpyrrolidinium chlorotrifluoroborate prepared in Example 4 and propylene carbonate.

TABLE 4

| | electrolyte (wt %) | PC (wt %) | electrical conductivity (25° C.) (mS/cm) | (0° C.) (mS/cm) | (−30° C.) (mS/cm) |
|---|---|---|---|---|---|
| Ex. 22 | 20 | 80 | 14.0 | 8.2 | 2.8 |
| | 40 | 60 | 17.2 | 9.3 | 2.7 |
| | 60 | 40 | 15.5 | 7.9 | 2.1 |
| | 80 | 20 | 12.2 | 5.5 | 1.2 |
| | 100 | 0 | 7.9 | 3.1 | 0.6 |

Example 23

The solutions were checked for electrical conductivity in the same manner as in Example 19 with the exception of using N-methoxymethyl-N-methylpyrrolidinium chlorotrifluoroborate prepared in Example 4 and ethylmethyl carbonate.

TABLE 5

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 23 | 70 | 30 | 14.7 | 7.6 | 2.0 |
| | 80 | 20 | 13.4 | 6.2 | 1.3 |
| | 100 | 0 | 7.9 | 3.1 | 0.6 |

Example 24

The solutions were checked for electrical conductivity in the same manner as in Example 19 with the exception of using N-methoxymethyl-N-methylpyrrolidinium tetrafluoroaluminate prepared in Example 5 and propylene carbonate.

TABLE 6

| | electrolyte (wt %) | PC (wt %) | electrical conductivity (25° C.) (mS/cm) | (0° C.) (mS/cm) | (−30° C.) (mS/cm) |
|---|---|---|---|---|---|
| Ex. 24 | 20 | 80 | 13.5 | 7.8 | 2.7 |
| | 40 | 60 | 16.5 | 9.2 | 2.6 |
| | 60 | 40 | 15.5 | 8.0 | 0.8 |
| | 80 | 20 | 12.9 | 3.4 | solid |
| | 100 | 0 | 7.1 | 0.1 | 0.005 |

Example 25

The solutions were checked for electrical conductivity in the same manner as in Example 19 with the exception of using N-methoxymethyl-N-methylpyrrolidinium tetrafluoroaluminate prepared in Example 5 and ethylmethyl carbonate.

TABLE 7

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 25 | 50 | 50 | 15.5 | 9.7 | solid |
| | 60 | 40 | 16.7 | 9.1 | solid |
| | 80 | 20 | 14.0 | 3.7 | solid |
| | 100 | 0 | 7.1 | 0.1 | 0.005 |

Example 26

The solutions were checked for electrical conductivity in the same manner as in Example 19 with the exception of using N-methoxymethyl-N-methylpyrrolidinium tetrafluoroaluminate prepared in Example 5, ethylene carbonate, propylene carbonate and dimethyl carbonate.

TABLE 8

| | electrolyte (wt %) | EC (wt %) | PC (wt %) | DMC (wt %) | electrical conductivity (25° C.) (mS/cm) | (−30° C.) (mS/cm) |
|---|---|---|---|---|---|---|
| Ex. 26 | 30 | 25 | 20 | 25 | 22.4 | 5.2 |
| | 40 | 20 | 20 | 20 | 23.6 | 3.5 |
| | 40 | 25 | 10 | 25 | 24.0 | 4.9 |
| | 45.3 | 27.5 | 18.1 | 9.1 | 22.4 | 2.0 |
| | 50 | 20 | 20 | 10 | 22.6 | 1.8 |

Example 27

The solutions were checked for electrical conductivity in the same manner as in Example 19 with the exception of using N-methoxymethyl-N-methylpyrrolidinium pentafluoroethyl trifluoroborate prepared in Example 6 and ethylmethyl carbonate.

TABLE 9

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 27 | 20 | 80 | 10.8 | 5.4 | 1.5 |
| | 40 | 60 | 12.6 | 7.4 | 2.3 |
| | 60 | 40 | 14.5 | 7.8 | 2.5 |
| | 80 | 20 | 11.7 | 5.4 | 1.4 |
| | 100 | 0 | 6.7 | 2.4 | 0.3 |

Example 28

The solutions were checked for electrical conductivity in the same manner as in Example 19 with the exception of using N-methoxymethyl-N-methylpyrrolidinium bis(fluorosulfonyl)imide prepared in Example 7 and propylene carbonate.

TABLE 10

| | electrolyte (wt %) | PC (wt %) | electrical conductivity (25° C.) (mS/cm) | (0° C.) (mS/cm) | (−30° C.) (mS/cm) |
|---|---|---|---|---|---|
| Ex. 28 | 20 | 80 | 11.6 | 6.8 | 2.4 |
| | 40 | 60 | 15.5 | 8.8 | 2.7 |
| | 50 | 50 | 15.7 | 8.7 | 2.7 |
| | 100 | 0 | 10.3 | 5.2 | 1.4 |

Example 29

The solutions were checked for electrical conductivity in the same manner as in Example 19 with the exception of using N-methoxymethyl-N-methylpyrrolidinium bis(fluorosulfonyl)imide prepared in Example 7 and dimethyl carbonate.

TABLE 11

| | electrolyte (wt %) | DMC (wt %) | electrical conductivity (25° C.) (mS/cm) | (0° C.) (mS/cm) | (−30° C.) (mS/cm) |
|---|---|---|---|---|---|
| Ex. 29 | 20 | 80 | 8.3 | solid | solid |
| | 40 | 60 | 21.3 | 14.5 | solid |
| | 60 | 40 | 23.8 | 15.3 | solid |
| | 80 | 20 | 17.5 | 9.8 | 3.1 |
| | 100 | 0 | 10.3 | 5.2 | 1.4 |

Example 30

The solutions were checked for electrical conductivity in the same manner as in Example 19 with the exception of using N-methoxymethyl-N-methylpyrrolidinium bis(fluorosulfonyl)imide prepared in Example 7 and ethylmethyl carbonate.

TABLE 12

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 30 | 20 | 80 | — | — | — |
| | 40 | 60 | 15.3 | 10.3 | 4.9 |
| | 60 | 40 | 18.7 | 11.6 | 4.5 |
| | 80 | 20 | 15.2 | 8.4 | 2.7 |
| | 100 | 0 | 10.3 | 5.2 | 1.4 |

Example 31

The solutions were checked for electrical conductivity in the same manner as in Example 19 with the exception of using N-methoxymethyl-N-methylpyrrolidinium hexafluorophosphate prepared in Example 8 and ethylmethyl carbonate.

TABLE 13

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 31 | 20 | 80 | — | — | — |
| | 40 | 60 | — | — | — |
| | 43 | 57 | 10.21 | 6.19 | 2.55 |

TABLE 13-continued

| electrolyte (wt %) | EMC (wt %) | electrical conductivity (25° C.) (mS/cm) | (0° C.) (mS/cm) | (−30° C.) (mS/cm) |
|---|---|---|---|---|
| 47 | 53 | 10.91 | 6.42 | 2.41 |
| 55 | 45 | 11.28 | 6.28 | 2.28 |
| 60 | 40 | 11.06 | 5.94 | 1.90 |
| 80 | 20 | 6.99 | 3.03 | solid |

Example 32

Figure 6:
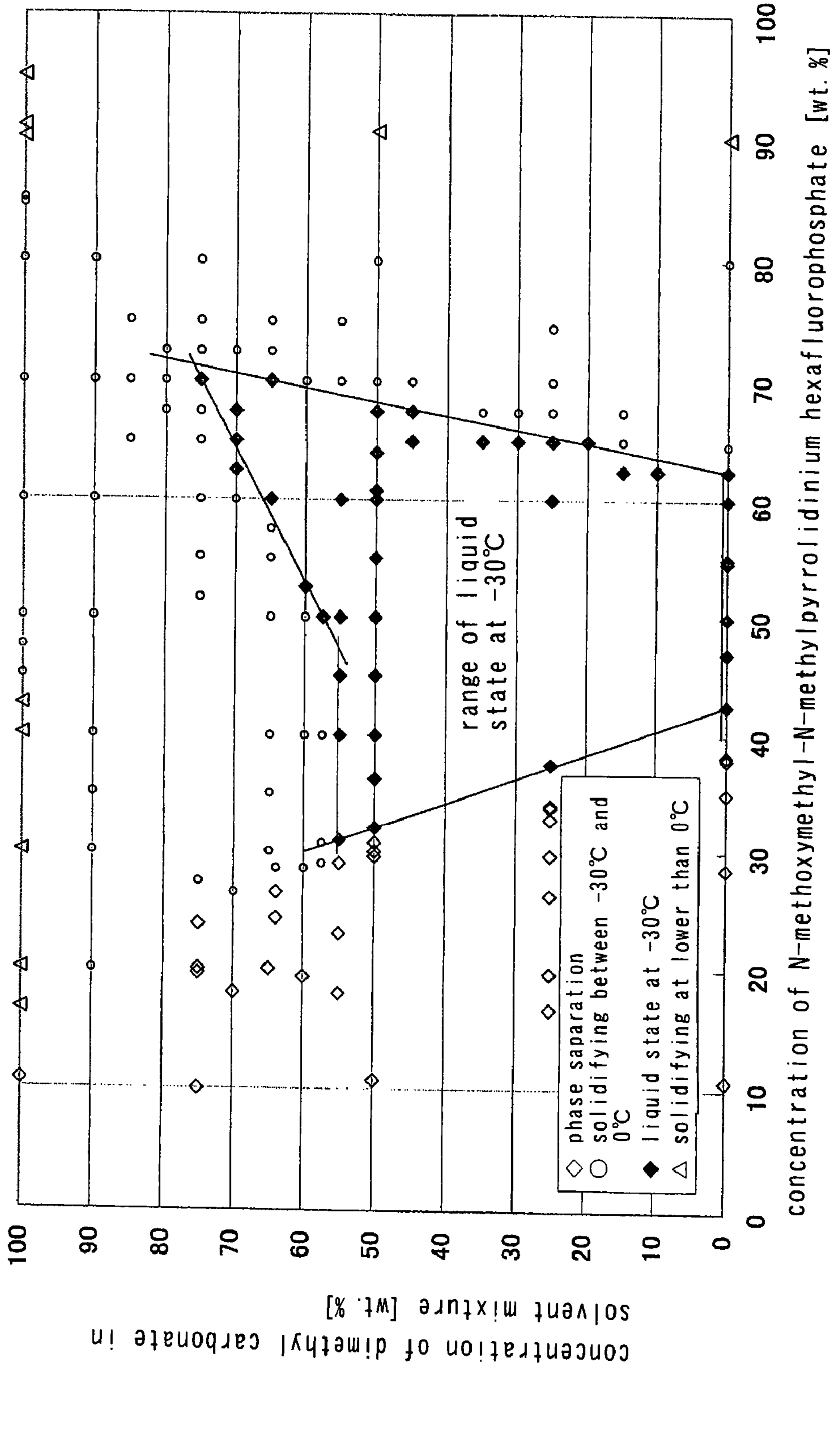
FIG. 6 is a graph showing a relationship of ratio, temperature and state of the composition of the invention.

The N-methoxymethyl-N-methylpyrrolidinium haxafluorophosphate prepared in Example 8, ethylmethyl carbonate and dimethyl carbonate were mixed together within a dry box having a nitrogen atmosphere, up to −60° C. in dew point, to obtain solutions having varying concentrations. Each of glass vessels containing a solution was taken out from the dry box and immersed in a constant-temperature bath. The solutions were classified into those maintaining liquid state at −30° C., those solidifying between −30° C. and 0° C., those solidifying at lower than 0° C. and those causing phase separation. FIG. 6 shows a relation between concentrations of N-methoxymethyl-N-methylpyrrolidinium hexafluorophosphate, ethylmethyl carbonate and dimethyl carbonate, and observation results with unaided eye. In FIG. 6, horizontal axis shows a concentration of N-methoxymethyl-N-methylpyrrolidinium hexafluorophosphate, vertical axis weight ratio of dimethyl carbonate in a mixture of ethylmethyl carbonate and dimethyl carbonate. For example, a line wherein a value of vertical axis is zero means the solvent is only ethylmethyl carbonate.

Further, in FIG. 6, provided that the concentration of N-methoxymethyl-N-methylpyrrolidinium hexafluorophosphate is shown with X, the weight ratio of dimethyl carbonate in a solvent mixture is shown with Y, the range represented by the following equations is liquid state at −30° C.

(when X<46.87)

$$Y \geqq -4.7X + 202.0$$

$$Y \geqq 0$$

$$Y \leqq 55.0$$

(when 46.87≦X)

$$Y \leqq 0.88X + 13.75$$

$$8.67X - 541.7 \leqq Y$$

A part of the solutions were checked for electrical conductivity. Table 14 gives the results.

TABLE 14

| | electrolyte (wt %) | DMC (wt %) | EMC (wt %) | electrical conductivity (25° C.) (mS/cm) | (0° C.) (mS/cm) | (−30° C.) (mS/cm) |
|---|---|---|---|---|---|---|
| Ex. | 32 | 34 | 34 | 9.8 | 6.9 | 3.3 |
| 32 | 36 | 32 | 32 | 11.5 | 7.6 | 3.3 |
| | 40 | 35 | 35 | 12.7 | 8.3 | 3.5 |
| | 45 | 27.5 | 27.5 | 13.7 | 8.7 | 3.5 |
| | 55 | 22.5 | 22.5 | 14.4 | 8.4 | 2.9 |
| | 60 | 20 | 20 | 13.3 | 7.3 | 2.4 |
| | 37.5 | 15.5 | 46.5 | 10.4 | 6.8 | 3.0 |
| | 32 | 37.4 | 30.6 | 11.5 | 7.6 | 3.4 |

TABLE 14-continued

| electrolyte (wt %) | DMC (wt %) | EMC (wt %) | electrical conductivity (25° C.) (mS/cm) | (0° C.) (mS/cm) | (−30° C.) (mS/cm) |
|---|---|---|---|---|---|
| 36.3 | 35.0 | 28.7 | 11.7 | 7.8 | 3.4 |
| 40 | 33 | 27 | 14.2 | 8.0 | 3.4 |
| 42.5 | 31.6 | 25.9 | 13.7 | 8.7 | 3.8 |
| 45 | 30.3 | 24.7 | 14.7 | 8.9 | 3.7 |
| 50 | 27.5 | 22.5 | 15.0 | 9.1 | 3.4 |
| 60 | 26 | 14 | 12.5 | 7.8 | 2.6 |
| 67.5 | 22.3 | 10.2 | 11.7 | 6.5 | 1.8 |
| 70 | 22.5 | 7.5 | 12.1 | 6.1 | 1.6 |
| 67.5 | 16.25 | 16.25 | 11.8 | 5.2 | 1.7 |
| 65 | 8.5 | 26.2 | 12.8 | 7.5 | 2.8 |

Example 33

The solutions were checked for electrical conductivity in the same manner as in Example 19 with the exception of using N-methoxymethyl-N-methylpyrrolidinium arsenate prepared in Example 9 and ethylmethyl carbonate.

TABLE 15

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 33 | 20 | 80 | — | — | — |
| | 40 | 60 | 9.55 | 6.10 | 3.01 |
| | 60 | 40 | 11.79 | 6.63 | 2.33 |
| | 80 | 20 | 4.74 | 3.32 | solid |

Example 34

The solutions were checked for electrical conductivity in the same manner as in Example 19 with the exception of using N-methoxymethyl-N-methylpyrrolidinium antimonate prepared in Example 10 and ethylmethyl carbonate.

TABLE 16

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 34 | 20 | 80 | — | — | — |
| | 40 | 60 | 9.38 | 6.22 | 2.97 |
| | 60 | 40 | 13.66 | 8.03 | 3.10 |
| | 80 | 20 | 9.15 | 4.31 | 1.14 |

Example 35

The solutions were checked for electrical conductivity in the same manner as in Example 19 with the exception of using N-ethyl-N-methoxymethylpyrrolidinium chlorotrifluoroborate prepared in Example 11 and dimethyl carbonate.

TABLE 17

| | electrolyte (wt %) | DMC (wt %) | electrical conductivity (25° C.) (mS/cm) | (0° C.) (mS/cm) | (−30° C.) (mS/cm) |
|---|---|---|---|---|---|
| Ex. 35 | 40 | 60 | 17.0 | 11.0 | — |
| | 60 | 40 | 20.0 | 11.3 | — |
| | 80 | 20 | 14.7 | 7.2 | 1.6 |
| | 100 | 0 | 6.0 | 1.7 | solid |

Example 36

The solutions were checked for electrical conductivity in the same manner as in Example 19 with the exception of using N-ethyl-N-methoxymethylpyrrolidinium chlorotrifluoroborate prepared in Example 11 and ethylmethyl carbonate.

TABLE 18

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 36 | 20 | 80 | — | — | — |
| | 40 | 60 | — | — | — |
| | 60 | 40 | 14.2 | 8.0 | 2.5 |
| | 80 | 20 | 12.0 | 5.5 | 1.1 |
| | 100 | 0 | 6.0 | 1.7 | solid |

Example 37

The solutions were checked for electrical conductivity in the same manner as in Example 19 with the exception of using N-ethyl-N-methoxymethylpyrrolidinium tetrafluoroaluminate prepared in Example 12 and propylene carbonate.

TABLE 19

| | electrolyte (wt %) | PC (wt %) | electrical conductivity (25° C.) (mS/cm) | (0° C.) (mS/cm) | (−30° C.) (mS/cm) |
|---|---|---|---|---|---|
| Ex. 37 | 20 | 80 | 13.5 | 7.9 | 2.7 |
| | 40 | 60 | 16.6 | 9.1 | 2.8 |
| | 60 | 40 | 15.6 | 8.1 | 2.1 |
| | 80 | 20 | 11.7 | 5.5 | 0.7 |
| | 100 | 0 | 7.3 | 2.5 | solid |

Example 38

The solutions were checked for electrical conductivity in the same manner as in Example 19 with the exception of using N-ethyl-N-methoxymethylpyrrolidinium tetrafluoroaluminate prepared in Example 12 and dimethyl carbonate.

TABLE 20

| | electrolyte (wt %) | DMC (wt %) | electrical conductivity (25° C.) (mS/cm) | (0° C.) (mS/cm) | (−30° C.) (mS/cm) |
|---|---|---|---|---|---|
| Ex. 38 | 40 | 60 | 17.6 | 11.4 | — |
| | 60 | 40 | 19.6 | 11.2 | — |
| | 80 | 20 | 14.7 | 6.9 | 1.6 |
| | 100 | 0 | 7.3 | 2.5 | solid |

Example 39

The solutions were checked for electrical conductivity in the same manner as in Example 19 with the exception of using N-ethyl-N-methoxymethylpyrrolidinium tetrafluoroaluminate prepared in Example 12 and ethylmethyl carbonate.

TABLE 21

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 39 | 20 | 80 | — | — | — |
| | 40 | 60 | — | — | — |
| | 60 | 40 | 14.8 | 8.2 | 2.7 |
| | 80 | 20 | 11.9 | 5.4 | 1.1 |
| | 100 | 0 | 7.3 | 2.5 | solid |

Example 40

The solutions were checked for electrical conductivity in the same manner as in Example 19 with the exception of using N-ethyl-N-methoxymethylpyrrolidinium tetrafluoroaluminate prepared in Example 12, ethylene carbonate, propylene carbonate and dimethyl carbonate.

TABLE 22

| | electrolyte (wt %) | EC (wt %) | PC (wt %) | DMC (wt %) | electrical conductivity (25° C.) (mS/cm) | (0° C.) (mS/cm) | (−30° C.) (mS/cm) |
|---|---|---|---|---|---|---|---|
| Ex. 40 | 40 | 25 | 10 | 25 | 24.0 | 15.1 | 5.8 |

Example 41

The solutions were checked for electrical conductivity in the same manner as in Example 19 with the exception of using N-ethyl-N-methoxymethylpyrrolidinium hexafluorophosphate prepared in Example 13 and dimethyl carbonate.

TABLE 23

| | electrolyte (wt %) | DMC (wt %) | electrical conductivity (25° C.) (mS/cm) | (0° C.) (mS/cm) | (−30° C.) (mS/cm) |
|---|---|---|---|---|---|
| Ex. 41 | 40 | 60 | 16.2 | 10.6 | solid |
| | 60 | 40 | 15.4 | 8.6 | solid |
| | 80 | 20 | 8.0 | 3.3 | solid |

Example 42

The solutions were checked for electrical conductivity in the same manner as in Example 19 with the exception of using N-ethyl-N-methoxymethylpyrrolidinium hexafluorophosphate prepared in Example 13 and ethylmethyl carbonate.

TABLE 24

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 42 | 40 | 60 | 9.7 | 6.1 | 2.5 |
| | 60 | 40 | 10.7 | 5.8 | 1.8 |
| | 80 | 20 | 5.8 | 2.2 | solid |

Example 43

The solutions were checked for electrical conductivity in the same manner as in Example 19 with the exception of using N-ethyl-N-methoxymethylpyrrolidinium hexafluorophosphate prepared in Example 14 and dimethyl carbonate.

TABLE 25

| | electrolyte (wt %) | DMC (wt %) | electrical conductivity (25° C.) (mS/cm) | (0° C.) (mS/cm) | (−30° C.) (mS/cm) |
|---|---|---|---|---|---|
| Ex. 43 | 40 | 60 | 15.6 | 10.4 | solid |
| | 60 | 40 | 16.3 | 9.6 | solid |
| | 80 | 20 | 8.4 | 3.5 | solid |

Example 44

The solutions were checked for electrical conductivity in the same manner as in Example 19 with the exception of using N-ethyl-N-methoxymethylpyrrolidinium hexafluoroarsenate prepared in Example 14 and ethylmethyl carbonate.

TABLE 26

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 44 | 40 | 60 | 9.6 | 6.2 | 2.6 |
| | 60 | 40 | 11.5 | 6.6 | 2.3 |
| | 80 | 20 | 6.7 | 2.8 | solid |

Example 45

The solutions were checked for electrical conductivity in the same manner as in Example 19 with the exception of using N-ethoxymethyl-N-methylpyrrolidinium chlorotrifluoroborate prepared in Example 15 and dimethyl carbonate.

TABLE 27

| | electrolyte (wt %) | DMC (wt %) | electrical conductivity (25° C.) (mS/cm) | (0° C.) (mS/cm) | (−30° C.) (mS/cm) |
|---|---|---|---|---|---|
| Ex. 45 | 40 | 60 | 15.1 | 9.6 | — |
| | 60 | 40 | 16.9 | 9.5 | — |
| | 80 | 20 | 12.2 | 5.5 | 1.1 |
| | 100 | 0 | 5.3 | 2.1 | solid |

Example 46

The solutions were checked for electrical conductivity in the same manner as in the same manner as in Example 19 with the exception of using N-ethoxymethyl-N-methylpyrrolidinium chlorotrifluoroborate prepared in Example 15 and ethylmethyl carbonate.

TABLE 28

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 46 | 20 | 80 | — | — | — |
| | 40 | 60 | — | — | — |
| | 60 | 40 | 12.1 | 6.7 | 2.0 |
| | 80 | 20 | 10.0 | 4.5 | 0.9 |
| | 100 | 0 | 5.3 | 2.1 | solid |

Example 47

The solutions were checked for electrical conductivity in the same manner as in Example 19 with the exception of using N-ethoxymethyl-N-methylpyrrolidinium tetrafluoroaluminate prepared in Example 16 and propylene carbonate.

TABLE 29

| | electrolyte (wt %) | PC (wt %) | electrical conductivity (25° C.) (mS/cm) | (0° C.) (mS/cm) | (−30° C.) (mS/cm) |
|---|---|---|---|---|---|
| Ex. 47 | 20 | 80 | 13.3 | 7.7 | 2.7 |
| | 40 | 60 | 16.3 | 9.2 | 2.8 |
| | 60 | 40 | 15.0 | 8.0 | 1.1 |
| | 80 | 20 | 11.9 | 4.4 | 0.1 |
| | 100 | 0 | 7.7 | 0.5 | solid |

Example 48

The solutions were checked for electrical conductivity in the same manner as in Example 19 with the exception of using N-ethoxymethyl-N-methylpyrrolidinium tetrafluoroaluminate prepared in Example 16 and dimethyl carbonate.

TABLE 30

| | electrolyte (wt %) | DMC (wt %) | electrical conductivity (25° C.) (mS/cm) | (0° C.) (mS/cm) | (−30° C.) (mS/cm) |
|---|---|---|---|---|---|
| Ex. 48 | 40 | 60 | 19.2 | 12.8 | solid |
| | 60 | 40 | 22.0 | 13.3 | solid |
| | 80 | 20 | 15.1 | 6.4 | solid |
| | 100 | 0 | 7.7 | 0.5 | solid |

Example 49

The solutions were checked for electrical conductivity in the same manner as in Example 19 with the exception of using N-ethoxymethyl-N-methylpyrrolidinium tetrafluoroaluminate prepared in Example 16 and ethylmethyl carbonate.

TABLE 31

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 49 | 20 | 80 | — | — | — |
| | 40 | 60 | 12.8 | 8.2 | — |
| | 60 | 40 | 15.5 | 9.0 | 1.3 |
| | 80 | 20 | 13.2 | 5.5 | 0.2 |
| | 100 | 0 | 7.7 | 0.5 | solid |

Example 50

The solutions were checked for electrical conductivity in the same manner as in Example 19 with the exception of using N-ethoxymethyl-N-methylpyrrolidinium tetrafluoroaluminate prepared in Example 16, ethylene carbonate, propylene carbonate and dimethyl carbonate.

TABLE 32

| | electrolyte (wt %) | EC (wt %) | PC (wt %) | DMC (wt %) | electrical conductivity (25° C.) (mS/cm) | (0° C.) (mS/cm) | (−30° C.) (mS/cm) |
|---|---|---|---|---|---|---|---|
| Ex. 50 | 40 | 25 | 10 | 25 | 22.6 | 13.8 | 4.8 |

Example 51

The solutions were checked for electrical conductivity in the same manner as in Example 19 with the exception of using N-ethoxymethyl-N-methylpyrrolidinium hexafluorophosphate prepared in Example 17 and dimethyl carbonate.

TABLE 33

| | electrolyte (wt %) | DMC (wt %) | electrical conductivity (25° C.) (mS/cm) | (0° C.) (mS/cm) | (−30° C.) (mS/cm) |
|---|---|---|---|---|---|
| Ex. 51 | 40 | 60 | 14.6 | 8.3 | solid |
| | 60 | 40 | 14.7 | 9.7 | solid |
| | 80 | 20 | 7.8 | 3.2 | 0.6 |

Example 52

The solutions were checked for electrical conductivity in the same manner as in Example 19 with the exception of using N-ethoxymethyl-N-methylpyrrolidinium hexafluorophosphate prepared in Example 17 and ethylmethyl carbonate.

TABLE 34

| | electrolyte (wt %) | EMC (wt %) | electrical conductivity (25° C.) (mS/cm) | (0° C.) (mS/cm) | (−30° C.) (mS/cm) |
|---|---|---|---|---|---|
| Ex. 52 | 40 | 60 | 10.1 | 5.6 | 2.6 |
| | 60 | 40 | 8.8 | 5.6 | 1.6 |
| | 80 | 20 | 6.2 | 2.8 | 0.6 |

Example 53

The solutions were checked for electrical conductivity in the same manner as in Example 19 with the exception of using N-ethoxymethyl-N-methylpyrrolidinium hexafluorophosphate prepared in Example 18 and dimethyl carbonate.

TABLE 35

| | electrolyte (wt %) | DMC (wt %) | electrical conductivity (25° C.) (mS/cm) | (0° C.) (mS/cm) | (−30° C.) (mS/cm) |
|---|---|---|---|---|---|
| Ex. 53 | 40 | 60 | 15.3 | 10.3 | solid |
| | 60 | 40 | 17.0 | 10.4 | solid |
| | 80 | 20 | 8.6 | 4.1 | 1.0 |

Example 54

The solutions were checked for electrical conductivity in the same manner as in the same manner as in Example 19 with the exception of using N-ethoxymethyl-N-methylpyrrolidinium hexafluorophosphate prepared in Example 18 and ethylmethyl carbonate.

TABLE 36

| | electrolyte (wt %) | DMC (wt %) | electrical conductivity (25° C.) (mS/cm) | (0° C.) (mS/cm) | (−30° C.) (mS/cm) |
|---|---|---|---|---|---|
| Ex. 54 | 40 | 60 | 9.1 | 5.8 | 2.5 |
| | 60 | 40 | 10.8 | 6.0 | 2.0 |
| | 80 | 20 | 6.9 | 3.1 | 0.7 |

Comparative Example 1

Preparation of N-methoxyethyl-N-methylpyrrolidinium tetrafluoroborate

N-methylpyrrolidine (31.10 g, reagent, product of Tokyo Kasai Co., Ltd.) was dissolved in 124.30 g of toluene, followed by replacement with nitrogen. To the solution was added dropwise 61.22 g of bromoethyl methyl ether (reagent, product of Aldrich Corp.) at 27° C. over a period of 1 hour. The mixture was heated to a gradually raised temperature and then stirred at 60 to 70° C. for 37 hours to terminate the reaction. The reaction mixture was cooled to room temperature, and the resulting solids were filtered off under a nitrogen stream. The filter cake was washed with 70 g of toluene and thereafter dried in a vacuum (giving 78.99 g of a brown solid product). The solid product obtained was suspended in 200 g of acetone, and the suspension was stirred at room temperature, followed by washing with stirring at room temperature and filtration under a nitrogen stream. (This procedure was repeated twice.) The product was dried in a vacuum to result in a yield of 62.64 g. The product, which was colored, was dissolved in 131.83 g of water, 6.00 g of activated carbon (Carboraffin, product of Takeda Pharmaceutical Co., Ltd.) was added to the solution, and the mixture was stirred at 90 to 95° C. for 12 hours. The mixture was cooled to room temperature, and the activated carbon was separated off by filtration. The filtrate was concentrated in a vacuum, followed by drying in a vacuum to result in a yield of 58.34 g. The product was dissolved in a solvent mixture of 200.48 g of acetone and 27.22 g of chloroform with heating for recrystallization. The resulting white solids obtained were filtered off in a nitrogen stream, washed with 50 g of acetone and dried in a vacuum, giving 34.10 g of N-methoxyethyl-N-methylpyrrolidinium bromide.

$^1$H-NMR ($CD_3OD$) δ ppm: 2.24 (m 4H), 3.15 (s 3H), 3.40 (s 3H), 3.65 (m 6H), 3.83 (m 2H)

Subsequently, 40.0 g of the N-methoxyethyl-N-methylpyrrolidinium bromide prepared was dissolved in 40.0 g of MeOH, and 54.0 g of methanol solution of 30 wt. % $HBF_4$ was added to the solution. The mixture was heated at 130° C. in a nitrogen stream to remove hydrogen chloride produced as a by-product and an excess of $HBF_4$, giving 39.9 g of the desired product (white solid).

$^1$H-NMR ($CD_3OD$) δ ppm: 2.22 (m 4H), 3.10 (S 3H), 3.39 (S 3H), 3.58 (m 6H), 3.81 (m 2H)

The solutions were checked for electrical conductivity in the same manner as in Example 19 with the exception of using the above N-methoxyethyl-N-methylpyrrolidinium tetrafluoroborate and propylene carbonate.

TABLE 37

| | electrolyte (wt %) | PC (wt %) | electrical conductivity (25° C.) (mS/cm) |
|---|---|---|---|
| Com. Ex. 1 | 20 | 80 | 12.2 |
| | 40 | 60 | 13.0 |
| | 60 | 40 | 10.1 |
| | 80 | 20 | 6.3 |
| | 100 | 0 | 2.8 |

Comparative Example 2

The solutions were checked for electrical conductivity in the same manner as in Example 19 with the exception of using N-methoxyethyl-N-methylpyrrolidinium tetrafluoroborate prepared in Comparative Example 1 and ethylmethyl carbonate.

TABLE 38

| | | | electrical conductivity | | |
|---|---|---|---|---|---|
| | electrolyte (wt %) | EMC (wt %) | (25° C.) (mS/cm) | (0° C.) (mS/cm) | (−30° C.) (mS/cm) |
| Com. Ex. 2 | 20 | 80 | — | — | — |
| | 40 | 60 | — | — | — |
| | 60 | 40 | — | — | — |
| | 80 | 20 | 6.6 | 2.4 | 0.4 |
| | 100 | 0 | 2.8 | 0.7 | solid |

Comparative Example 3

Preparation of N,N,N-triethyl-N-methylammonium tetrafluoroborate ($TEMABF_4$)

A 100 g quantity of N,N,N-triethyl-N-methylammonium chloride (reagent, product of Tokyo Kasei Co., Ltd.) was dissolved in 100 g of methanol, and 200.0 g of a methanol solution of 30 wt. % $HBF_4$ was added to the solution. When the mixture was stirred for 30 minutes, crystals of N,N,N-triethyl-N-methylammonium tetrafluoroborate separated out. The mixture was filtered, and the crystals were washed with isopropyl alcohol and then dried in a nitrogen stream with heating at 130° C. to remove hydrogen chloride produced as a by-product, an excess of $HBF_4$, methanol and isopropyl alcohol, giving 127.1 g of the desired product (white solid).

$^1$H-NMR ($CD_3OD$) δ ppm: 1.31 (m 9H), 2.95 (S 3H), 3.34 (q 6H)

The solutions were checked for electrical conductivity in the same manner as in Example 19 with the exception of using N,N,N-triethyl-N-methylammonium tetrafluoroborate prepared above and ethylmethyl carbonate.

TABLE 39

| | | | electrical conductivity | | |
|---|---|---|---|---|---|
| | electrolyte (wt %) | EMC (wt %) | (25° C.) (mS/cm) | (0° C.) (mS/cm) | (−30° C.) (mS/cm) |
| Com. Ex. 3 | <1 | 99< | 0.0003 | — | — |

Comparison of Electrochemical Stability

Example 55

In a solution of a mixture of ethylmethyl carbonate and dimethyl carbonate (volume ratio=1:1) was dissolved N-methoxymethyl-N-methylpyrrolidinium hexafluorophosphate obtained in Example 8 at a concentration of 2 M, and the solution was checked for electrochemical stability. The compounds were mixed together within a dry box having a nitrogen atmosphere, up to −60° C. in dew point. The solutions prepared were checked for water content by a Karl Fischer moisture meter and found to be up to 30 ppm in water content.

Figure 7:
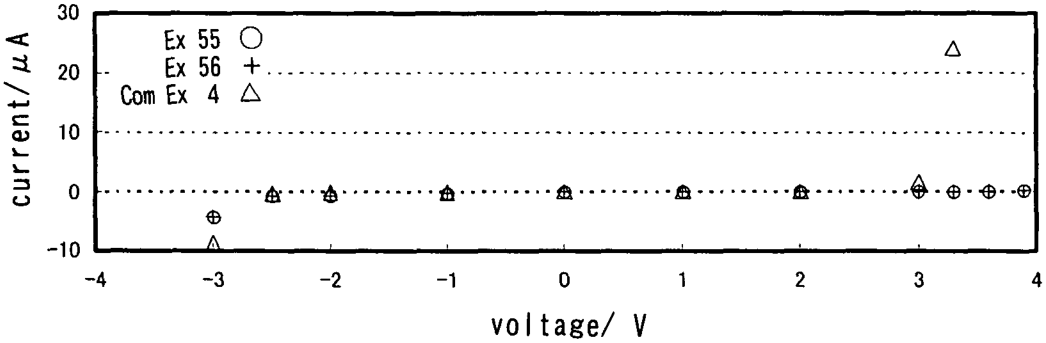
FIG. 7 is a graph showing an electrochemical stability of the composition of the invention.

The electrochemical stability was measured using a 3-pole electrochemical cell. Used as the working electrode was a glassy carbon electrode (product of BAS Inc.) 1.0 mm in diameter and 0.0079 $cm^{-2}$ in electrode area. The reference electrode used was a silver wire (product of the Nilaco Corp., 99.99% in purity). The counter electrode used was a platinum electrode (product of BAS Inc. 11-2233) measuring 0.5 mm in diameter and 50 mm in length. Constant voltage test was conducted to measure electrical current at 180 seconds after applying a specified voltage to the working electrode. FIG. 7 shows a relation of the current value and applied voltage.

Example 56

In ethylmethyl carbonate was dissolved N-methoxymethyl-N-methylpyrrolidinium hexafluorophosphate obtained in Example 8 at a concentration of 2 M, and the solution was checked for electrochemical stability. The compounds were mixed together within a dry box having a nitrogen atmosphere, up to −60° C. in dew point. The solutions prepared were checked for water content by a Karl Fischer moisture meter and found to be up to 30 ppm in water content.

The electrochemical stability was measured in the same manner as in Example 55 and the results were given in FIG. 7.

Comparative Example 4

In propylene carbonate was dissolved N,N,N-triethyl-N-methylammonium tetrafluoroborate obtained in Comparative Example 3 at a concentration of 1.5 M, and the solution was checked for electrochemical stability. The compounds were mixed together within a dry box having a nitrogen atmosphere, up to −60° C. in dew point. The solutions prepared were checked for water content by a Karl Fischer moisture meter and found to be up to 30 ppm in water content.

The electrochemical stability was measured in the same manner as in Example 55 and the results were given in FIG. 7.

Fabrication of Electric Double-Layer Capacitor

Example 57

In ethylmethyl carbonate was dissolved N-methoxymethyl-N-methylpyrrolidinium chlorotrifluoroborate obtained in Example 4 at a weight ratio of 30:70. The compounds were mixed together within a dry box having a nitrogen atmosphere, up to −60° C. in dew point. The solution prepared were checked for water content by a Karl Fischer moisture meter and found to be up to 30 ppm in water content.

An electric double-layer capacitor 1 having the construction of FIG. 1 was fabricated using the above electrolytic solution. Electrodes 1, 2 were made by kneading a conductive substance consisting mainly of activated carbon, binder and N-methylpyrrolidone to prepare a paste, coating aluminum foil with the paste to a thickness of 150 μm, thereafter drying the coating to obtain an electrode sheet and cutting out disks from the sheet. A container 1, container 2, spacer and spring were made of stainless steel, and a separator was made of a nonwoven polypropylene fabric. The capacitor was fabricated inside a glove box filled with argon gas. The electrodes 1, 2, containers 1, 2, spring and spacer were dried in a vacuum with heating at 120° C. for 24 hours and thereafter brought into the glove box. The electrodes 1, 2 and separator were impregnated with the above electrolytic solution for use in capacitors of the type mentioned, and the containers 1, 2 were crimped with a gasket provided therebetween to obtain the capacitor of the construction shown in FIG. 1.

Example 58

In propylene carbonate was dissolved N-methoxymethyl-N-methylpyrrolidinium tetrafluoroaluminate obtained in Example 5 at a weight ratio of 60:40 to obtain an electrolyte. The compounds were mixed together within a dry box having a nitrogen atmosphere, up to −70° C. in dew point. The solution prepared were checked for water content by a Karl Fischer moisture meter and found to be up to 30 ppm in water content.

An electric double-layer capacitor was prepared in the same manner as in Example 57 except of using the above electrolyte.

Example 59

In ethylmethyl carbonate was dissolved N-methoxymethyl-N-methylpyrrolidinium tetrafluoroaluminate obtained in Example 5 at a weight ratio of 40:60 to obtain an electrolyte. The compounds were mixed together within a dry box having a nitrogen atmosphere, up to −70° C. in dew point. The solution prepared were checked for water content by a Karl Fischer moisture meter and found to be up to 30 ppm in water content.

An electric double-layer capacitor was prepared in the same manner as in Example 57 except of using the above electrolyte.

Example 60

N-methoxymethyl-N-methylpyrrolidinium tetrafluoroaluminate obtained in Example 5, propylene carbonate, dimethyl carbonate and ethylmethyl carbonate were mixed at a weight ratio of 40:20:20:20 to obtain an electrolyte. The compounds were mixed together within a dry box having a nitrogen atmosphere, up to −70° C. in dew point. The solution prepared were checked for water content by a Karl Fischer moisture meter and found to be up to 30 ppm in water content.

An electric double-layer capacitor was prepared in the same manner as in Example 57 except of using the above electrolyte.

Example 61

An electric double-layer capacitor was prepared in the same manner as in Example 57 except of using the electrolyte obtained in Example 55.

Example 62

An electric double-layer capacitor was prepared in the same manner as in Example 57 except of using the electrolyte obtained in Example 56.

Comparative Example 5

An electric double-layer capacitor was prepared in the same manner as in Example 57 except of using the electrolyte obtained in Comparative Example 4.

[Measurement of Leak Electric Current Value]

The coin-shaped electric double-layer capacitors fabricated in Examples 57 to 62 and Comparative Example 5 were checked for leak electric current value at 25° C. A coin-shaped cell was set in a holder specific thereto and thereafter immersed in a constant-temperature bath so as to maintain the cell at a constant temperature. At this time, the holder is covered in its entirety with a vinyl bag so as to hold the cell out of contact with a refrigerant in the bath. The cell was held immersed in the bath as set at the specified temperature for 4 hours and the capacitor was thereafter brought into a charge-discharge operation. The capacitor was charged with constant current at a current density of 0.5 $mAcm^{-2}$, the constant-current charging was changed over to constant-voltage charging upon the voltage reaching 2.5 V, and the capacitor was held at 2.5 V for 300 minutes, followed by constant-current charging at 0.5 $mAcm^{-2}$. Upon the voltage dropping to 0 V, the charging was changed over to constant-voltage discharging, and the capacitor was held at 0 V for 300 minutes. Consequently, the capacitor was charged with constant current at a current density of 0.5 $mAcm^{-2}$, and the capacitor was held at 2.7 V for 300 minutes, followed by constant-current charging at 0.5 $mAcm^{-2}$. Upon the voltage dropping to 0 V, the charging was changed over to constant-voltage discharging, and the capacitor was held at 0 V for 300 minutes.

Thereafter, the same cycle as above was repeated twice with constant-voltage charging at 3.0 V and 3.3 V, respectively. An electric current 300 minutes after the constant-voltage charging was measured as a leak electric current value. Table 40 shows the results.

TABLE 40

| | leak electric current value (mA) | | | |
|---|---|---|---|---|
| | 2.5 V | 2.7 V | 3.0 V | 3.3 V |
| Ex. 57 | 0.015 | 0.018 | 0.018 | 0.043 |
| Ex. 58 | 0.012 | 0.013 | 0.015 | 0.020 |
| Ex. 59 | 0.011 | 0.012 | 0.013 | 0.016 |
| Ex. 60 | 0.011 | 0.014 | 0.015 | 0.019 |
| Ex. 61 | 0.013 | 0.010 | 0.015 | 0.044 |
| Ex. 62 | 0.011 | 0.012 | 0.015 | 0.041 |
| Com. Ex. 5 | 0.018 | 0.032 | 0.072 | 0.180 |

Measurement of iR Loss

Example 63

In propylene carbonate was dissolved N-methoxymethyl-N-methylpyrrolidinium chlorotrifluoroborate obtained in Example 4 at a weight ratio of 60:40 to obtain an electrolyte. The compounds were mixed together within a dry box having a nitrogen atmosphere, up to −70° C. in dew point. The solution prepared were checked for water content by a Karl Fischer moisture meter and found to be up to 30 ppm in water content.

An electric double-layer capacitor was prepared in the same manner as in Example 57 except of using the above electrolyte.

Example 64

In propylene carbonate was dissolved N-methoxymethyl-N-methylpyrrolidinium bis(fluorosulfonyl)imide obtained in Example 7 at a weight ratio of 60:40 to obtain an electrolyte. The compounds were mixed together within a dry box having a nitrogen atmosphere, up to −70° C. in dew point. The solution prepared were checked for water content by a Karl Fischer moisture meter and found to be up to 30 ppm in water content.

An electric double-layer capacitor was prepared in the same manner as in Example 57 except of using the above electrolyte.

The coin-shaped electric double-layer capacitors fabricated in Examples 58, 60, 63 and 64 and Comparative Example 5 were checked for iR loss value. The electric double-layer capacitors were brought into a charge-discharge operation at 0° C. in a constant-temperature bath. The capacitor was charged with constant current at a current density of 0.5 $mAcm^{-2}$, the constant-current charging was changed over to constant-voltage charging upon the voltage reaching 2.5 V, and the capacitor was held at 2.5 V for 90 minutes, followed by constant-current charging at 0.5 $mAm^{-2}$. Upon the voltage dropping to 0.1 V, the charging was changed over to constant-voltage discharging, and the capacitor was held at 0.1 V for 90 minutes. These charge and discharge steps were combined together as one cycle and iR loss value was measured immediately after discharging in the fourth cycle. The results were given in Table 41. For comparison, Table 14 shows iR loss values of Examples 58, 60, 63 and 64 relative to the iR loss value obtained in Comparative Example 5 immediately after discharging in the fourth cycle and taken as 100.

TABLE 41

| | iR loss |
|---|---|
| Ex. 58 | 75 |
| Ex. 60 | 51 |
| Ex. 63 | 75 |
| Ex. 64 | 79 |
| Com. Ex. 5 | 100 |

Fabrication of Electric Double-Layer Capacitor 2

Example 65

In ethylmethyl carbonate was dissolved N-methoxymethyl-N-methylpyrrolidinium pentafluoroethyl trifluoroborate obtained in Example 6 at a weight ratio of 40:60. The compounds were mixed together within a dry box having a nitrogen atmosphere, up to −60° C. in dew point. The solution prepared were checked for water content by a Karl Fischer moisture meter and found to be up to 30 ppm in water content.

Figure 3:
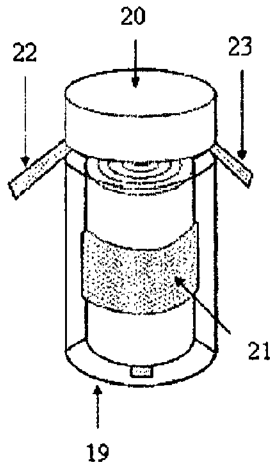
FIG. 3 is a diagrammatical view of beaker cell type electric double-layer capacitor.

An electric double-layer capacitor 2 having the construction of FIG. 3 was fabricated using the above electrolytic solution.

An electric double-layer capacitor 2 is composed by a cylindrical glass container 19, a cylindrical screw cap 20, an electrode roll 21, striplike electric lead 22, 23 and an electrolytic solution.

Figure 4:
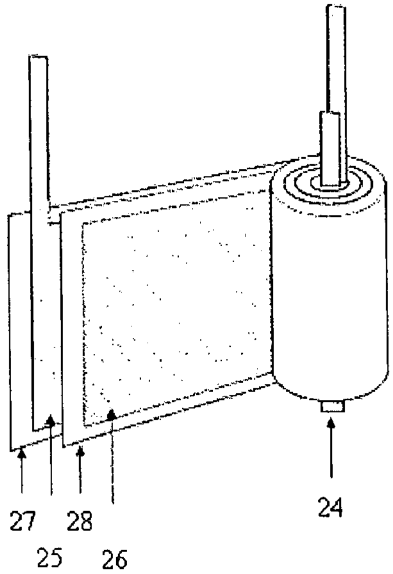
FIG. 4 is a development view of an electrode roll 21 of beaker cell type electric double-layer capacitor.

As shown in FIG. 4, the electrode roll 21 comprises a core made of fluorinated resin 24, a striplike positive electrode sheet 25, a striplike negative electrode sheet 26, and two striplike separators 27, 28 having sandwiched therebetween the positive electrode sheet 25. The electrode 3 is formed by winding these components in the order shown in FIG. 4 around the core 24 spirally, and fixed with fluorinated resin tape.

Positive electrode sheet 25 and negative electrode sheet 26 were made by kneading a conductive substance consisting mainly of activated carbon, binder and N-methylpyrrolidone to prepare a paste, coating aluminum foil having a thickness of 30 μm with the paste to a thickness of 150 μm, thereafter drying the coating. FIG. 4 shows a development view of the positive electrode sheet 25 and negative electrode sheet 26, providing striplike electric lead having no electrode layer.

The above components are thoroughly dried in a vacuum and are fabricated into an electric double-layer capacitor 2 as stated below in a dry box having a nitrogen atmosphere, up to −60° C. in dew point. Namely, the electrode roll 21 is placed into the cylindrical glass container 19, and an electrolytic solution obtained in Example 13 is injected into the container. In order to have the electrolytic solution penetrate into inside of the electrodes, the injection is conducted in a dry pass box in a vacuum. The spriplike electric leads are provided by tightly sealing the cylindrical glass container with the cylindrical screw cap 20, via fluorinated resin seal tape at a screw seal portion of the cylindrical glass container.

The above electric double-layer capacitors was checked for charge-discharge test and leak electric current value. The both tests were conducted in a dry box having a nitrogen atmosphere. The electric double-layer capacitor was brought into a charge-discharge operation under the following conditions. The capacitor was charged with constant current at a current density of 0.5 $mAcm^{-2}$, the constant-current charging was changed over to constant-voltage charging upon the voltage reaching 2.5 V, and the capacitor was held at 2.5 V for 300 minutes, followed by constant-current charging at 0.5 $mAcm^{-2}$. Upon the voltage dropping to 0 V, the charging was changed over to constant-voltage discharging, and the capacitor was held at 0 V for 300 minutes. The capacitance was calculated from the accumulated value of electric energy discharged.

The capacitor was checked for leak electric current value under the following conditions. The capacitor was charged with constant current at a current density of 0.5 $mAcm^{-2}$, the constant-current charging was changed over to constant-voltage charging upon the voltage reaching 2.7 V, and the capacitor was held at 2.7 V for 120 minutes, followed by constant-current charging at 0.5 $mAcm^{-2}$. Upon the voltage dropping to 3.0 V, the charging was changed over to constant-voltage discharging, and the capacitor was held for 120 minutes.

Thereafter, the same cycle as above was repeated twice with constant-voltage charging at 3.3 V and 3.6 V, respectively. An electric current 120 minutes after the constant-voltage charging was measured as a leak electric current value. Table 42 shows the results.

Comparative Example 6

An electric double-layer capacitor 2 was prepared in the same manner as in Example 65 except of using the electrolyte obtained in Comparative Example 4. The charge-discharge test and leak electric current value were measured in the same manner as in Example 57.

TABLE 42

| | leak electric current value (mA) | | | | |
|---|---|---|---|---|---|
| | 2.5 V | 2.7 V | 3.0 V | 3.3 V | 3.6 V |
| Ex. 65 | 0.208 | 0.231 | 0.247 | 0.357 | 0.614 |
| Com. Ex. 6 | 0.257 | 0.278 | 0.285 | 0.450 | 0.830 |

Example 66

In a solution of a mixture of ethylene carbonate (EC) and ethylmethyl carbonate (EMC)(volume ratio of EC:EMC=1:3) was dissolved N-methoxymethyl-N-methylpyrrolidinium pentafluoroethyl trifluoroborate obtained in Example 6 at a concentration of 30 wt. %, and thereto was added lithium tetrafluoroborate ($LiBF_4$) at a concentration of 0.6 M. The compounds were mixed together within a dry box having a nitrogen atmosphere, up to −60° C. in dew point. The solutions prepared were checked for water content by a Karl Fischer moisture meter and found to be up to 30 ppm in water content.

[Fabrication of Lithium Secondary Cell]

Figure 2:
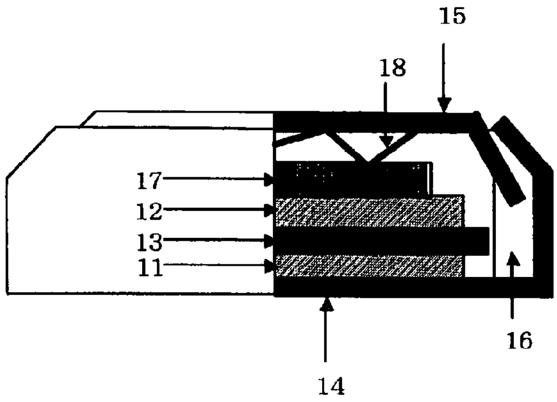
FIG. 2 is a sectional view showing a lithium secondary cell.
Figure 5:
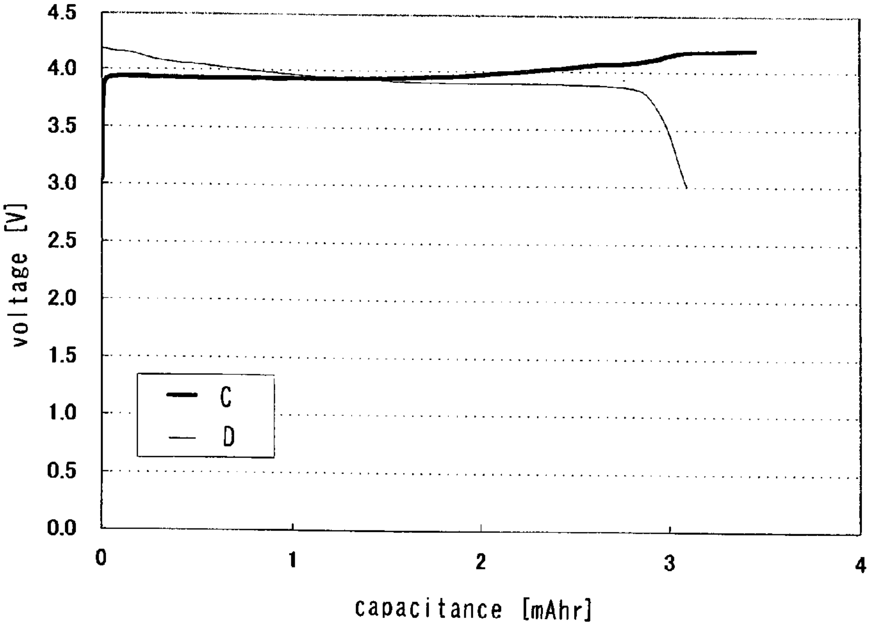
FIG. 5 shows charge-discharge curve measured with a coin-shaped lithium secondary battery.

FIG. 2 shows a coin-shaped lithium secondary cell. With reference to FIG. 2, indicated at 11 is a positive electrode, at 12 a negative electrode, at 13 a porous separator, at 14 a positive electrode can, at 15 a negative electrode can, at 16 a gasket, at 17 a spacer, and at 18 a spring. The lithium secondary cell shown in FIG. 2 was fabricated by the following procedure. The positive electrode can 14, negative electrode can 15, spacer 17 and spring 18 used were made of stainless steel. The negative electrode 12 used was made from metal lithium foil having a thickness of 200 μm, by cutting out a circular shape. To make the positive electrode 11, a powder of $LiCoO_2$, acetylene black serving as an auxiliary conductive agent and PVdF serving as a binder were mixed together in the ratio of 85:10:5, and the mixture was made into a paste with addition of N-methylpyrrolidone. Aluminum foil, 30 μm in thickness, was uniformly coated with the paste with an applicator for use in electrode coating. The coated foil was then dried in a vacuum at 120° C. for 8 hours and cut out in a circular shape by an electrode blanking machine to obtain the positive electrode 11. The separator and the blanked-out positive electrode were impregnated with the electrolytic solution obtained in Example 66. The positive electrode was placed on the bottom wall of the positive electrode can 14, the porous separator 13 was placed on the electrode, and the gasket 16 was placed into the can 14. The negative electrode 12, spacer 17, spring 18 and negative electrode can 15 were placed one after another over the porous separator 13, and an opening portion of the positive electrode can 14 was inwardly folded using a cell crimping machine to seal off the opening and fabricate a lithium secondary cell. The cells thus fabricated were subjected to a charge-discharge test in the following manner. Each cell was charged with a constant current of 0.21 mA, and upon the voltage reaching 4.2 V, the cell was charged with a constant voltage of 4.2 V for 30 minutes. The cell was discharged to voltage of 3 V at constant current of 0.21 mA. Upon the voltage reaching voltage of 3 V, the cell was held at 3 V for 30 minutes. These charge and discharge steps were combined together as one cycle. FIG. 5 shows the charge-discharge curve obtained in Example 66.

INDUSTRIAL APPLICABILITY

A quaternary ammonium salt of the formula (1), and an electrolytic solution containing the salt of the present invention are highly electrically conductive, highly soluble in chain carbonic acid esters which is high in voltage resistance, highly reliable at low temperatures and high in voltage resistance, and are suitable for an electrolyte for electrochemical device.

The invention claimed is:

1. A quaternary ammonium salt of the formula (1)

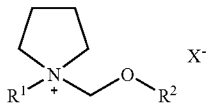

(1)

wherein $R^1$ is straight-chain or branched alkyl having 1 to 4 carbon atoms, $R^2$ is straight-chain or branched alkyl having 1 to 3 carbon atoms, and $X^-$ is $ClBF_3^-$, $AlF_4^-$, or $N(SO_2F)_2^-$.

2. A quaternary ammonium salt according to claim 1 wherein $R^1$ is alkyl having 1 to 2 carbon atoms, $R^2$ is alkyl having 1 to 2 carbon atoms, and $X^-$ is $ClBF_3^-$, $AlF_4^-$, or $N(SO_2F)_2^-$.

3. A quaternary ammonium salt of the formula (2)

(2)

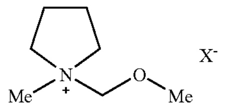

wherein $X^-$ is $ClBF_3^-$, $AlF_4^-$, or $N(SO_2F)_2^-$, and Me is methyl.

4. A quaternary ammonium salt according to claim 3 wherein $X^-$ is $AlF_4^-$ or $N(SO_2F)_2^-$.

5. A composition wherein the composition comprises at least the quaternary ammonium salt of claim 1 and an organic solvent.

6. A composition according to claim 5 wherein the organic solvent is chain carbonic acid esters.

7. A composition according to claim 6 wherein the chain carbonic acid ester is at least one selected from among ethylmethyl carbonate and dimethyl carbonate.

8. A composition according to claim 7 wherein the chain carbonic acid ester is ethylmethyl carbonate.

9. An electrolytic solution wherein the solution comprises an electrolyte of the formula (3)

(3)

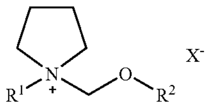

wherein $R^1$ is straight-chain or branched alkyl having 1 to 4 carbon atoms, $R^2$ is straight-chain or branched alkyl having 1 to 3 carbon atoms, and X— is $ClBF_3^-$, $AlF_4^-$, or $N(SO_2F)_2^-$.

10. The electrolytic solution of claim 9 wherein the solution comprises an organic solvent.

11. The electrolytic solution according to claim 10 wherein the organic solvent is a chain carbonic acid ester.

12. The electrolytic solution according to claim 11 wherein the chain carbonic acid ester is selected from the group consisting of: ethylmethyl carbonate and dimethyl carbonate.

13. The electrolytic solution according to claim 12 wherein the chain carbonic acid ester is ethylmethyl carbonate.

14. The electrolytic solution according to claim 10 wherein the organic solvent is a cyclic carbonic acid ester.

15. An electrochemical device comprising the electrolytic solution of claim 10.

16. An electric double-layer capacitor comprising the electrolytic solution of claim 10.

17. A secondary cell comprising the electrolytic solution of claim 10.

18. A process for preparing a quaternary ammonium salt of the formula (1)

(1)

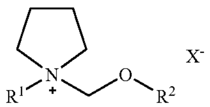

wherein $R^1$ is straight-chain or branched alkyl having 1 to 4 carbon atoms, $R^2$ is straight-chain or branched alkyl having 1 to 3 carbon atoms, and X— is $ClBF_3^-$, $AlF_4^-$, or $N(SO_2F)_2^-$, comprising (a) a step of reacting an alkylpyrrolidine of the formula (5) and a compound of the formula (6) to prepare a quaternary ammonium salt of the formula (1a)

(5)

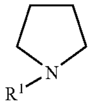

($R^1$ is same as defined above)

(6)

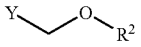

($R^2$ is same as defined above and Y Cl, Br or I)

(1a)

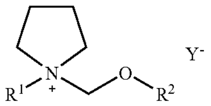

($R^1$, $R^2$ and Y are same as defined above), and (b) a step of reacting the quaternaryammonium salt of the formula (1a) and a compound of the formula (7)

MX (7)

(M is hydrogen, alkali metal atom, alkaline-earth metal atom or metal atom, and $X^-$ is same as defined above).

19. A process for preparing a quaternary ammonium salt of the formula (9) wherein a quaternary ammonium salt of the formula (8) is reacted with $BF_3$ (8)

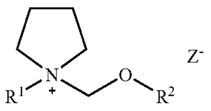

(9)

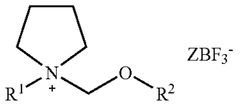

wherein $R^1$ is straight-chain or branched alkyl having 1 to 4 carbon atoms, $R^2$ is straight-chain or branched alkyl having 1 to 3 carbon atoms, Z is Cl.

20. A process for preparing a quaternary ammonium salt of the formula (11) wherein a quaternary ammonium salt of the formula (10) is reacted with $AlF_3$
(10)
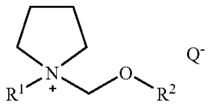
-continued
(11)
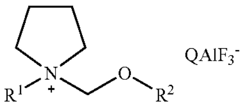
[wherein $R^1$ is straight-chain or branched alkyl having 1 to 4 carbon atoms, $R^2$ is straight-chain or branched alkyl having 1 to 3 carbon atoms, Q is F(HF)n (0≦n≦∞)].
* * * * *